United States Patent
Strehl

(10) Patent No.: US 10,980,916 B2
(45) Date of Patent: *Apr. 20, 2021

(54) METHODS OF PREPARING PERSONALIZED BLOOD VESSELS

(71) Applicant: VeriGraft AB, Gothenburg (SE)

(72) Inventor: Raimund Strehl, Gothenburg (SE)

(73) Assignee: VeriGraft AB, Gothenburg (SE)

(*) Notice: Subject to any disclaimer, the term of this patent is extended or adjusted under 35 U.S.C. 154(b) by 0 days.

This patent is subject to a terminal disclaimer.

(21) Appl. No.: 16/577,421

(22) Filed: Sep. 20, 2019

(65) Prior Publication Data

US 2020/0038556 A1 Feb. 6, 2020

Related U.S. Application Data

(63) Continuation of application No. 16/529,973, filed on Aug. 2, 2019.

(60) Provisional application No. 62/714,200, filed on Aug. 3, 2018.

(51) Int. Cl.
| | |
|---|---|
| *A61L 27/50* | (2006.01) |
| *C12M 1/12* | (2006.01) |
| *A61L 27/36* | (2006.01) |
| *A61L 27/54* | (2006.01) |
| *A61L 27/38* | (2006.01) |
| *A61L 33/00* | (2006.01) |
| *C12M 3/00* | (2006.01) |
| *C12M 1/00* | (2006.01) |
| *C12M 1/34* | (2006.01) |
| *G01N 33/66* | (2006.01) |

(52) U.S. Cl.
CPC ......... *A61L 27/507* (2013.01); *A61L 27/3687* (2013.01); *A61L 27/3804* (2013.01); *A61L 27/3882* (2013.01); *A61L 27/54* (2013.01); *A61L 33/0011* (2013.01); *C12M 21/08* (2013.01); *C12M 25/14* (2013.01); *C12M 29/00* (2013.01); *C12M 41/26* (2013.01); *C12M 41/30* (2013.01); *C12M 41/34* (2013.01); *G01N 33/66* (2013.01); *A61L 2300/21* (2013.01); *A61L 2300/232* (2013.01); *A61L 2300/236* (2013.01); *A61L 2300/414* (2013.01); *A61L 2300/42* (2013.01); *A61L 2430/40* (2013.01)

(58) Field of Classification Search
CPC .............................. A61L 27/507; C12M 25/14
See application file for complete search history.

(56) References Cited

FOREIGN PATENT DOCUMENTS

WO    WO 2013/136184 A2    9/2013

OTHER PUBLICATIONS

MSDS-Steen Solution, XVIVO Perfusion, available at http://www.xvivoperfusion.com/wp-content/uploads/2015/12/STEEN-Solution_2017_web.pdf (Year: 2000).*
Olausson et al. "In Vivo Application of Tissue-Engineered Veins Using Autologous Peripheral Whole Blood: A Proof of Concept Study" (2014), EBioMedicine, vol. 1: 72-79 (Year: 2014).*
Rambol et al. "Recellularizatin of Decellularized Venous Grafts Using Peripheral Blood: A Critical Evaluation" 2018, EBioMedicine, vol. 32: 215-222. (Year: 2018).*
Kuna et al., "Decellularization and Recellularization Methodology for Human Saphenous Veins," Journal of Visualized Experiments, Jul. 27, 2018, 137:e57803, 8 pages.

* cited by examiner

*Primary Examiner* — Teresa E Knight
(74) *Attorney, Agent, or Firm* — Foley & Lardner LLP

(57) ABSTRACT

The present disclosure relates to methods of preparing personalized blood vessels, useful for transplantation with improved host compatibility and reduced susceptibility to thrombosis. Also provided are personalized blood vessels produced by the methods and use thereof in surgery.

20 Claims, 5 Drawing Sheets

FIG. 1A  
Sham
FIG. 1B  
P-TEV
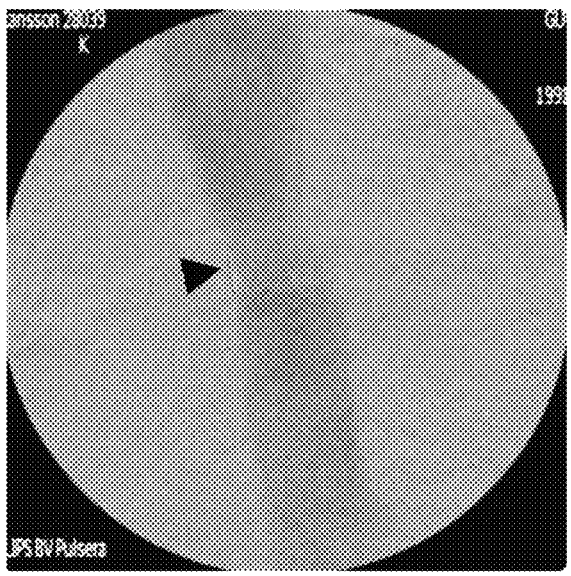
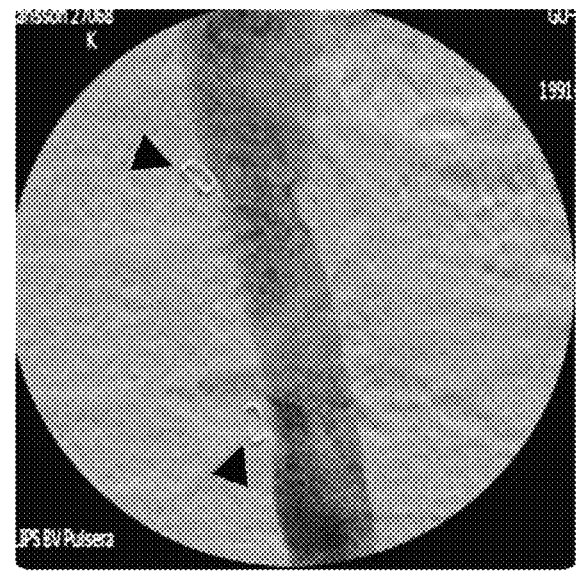

*Vena cava* cellularization two weeks post-surgery

*Vena cava* cellularization four weeks post-surgery
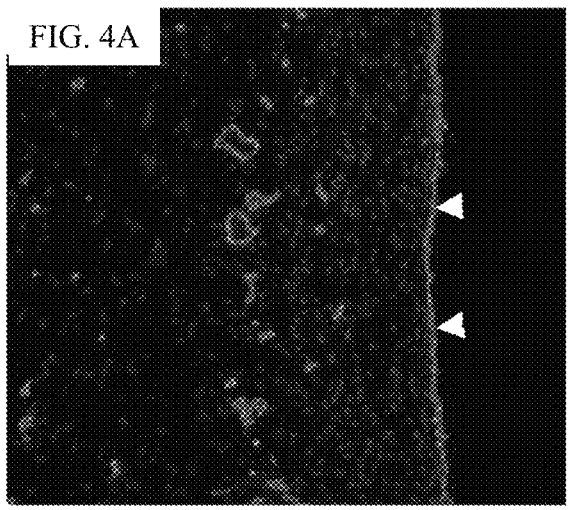
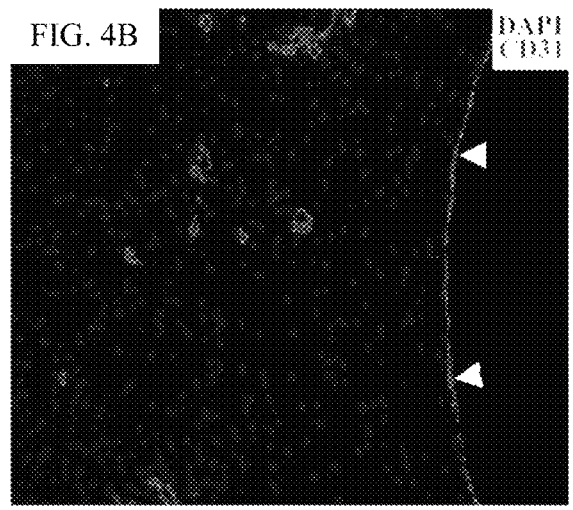
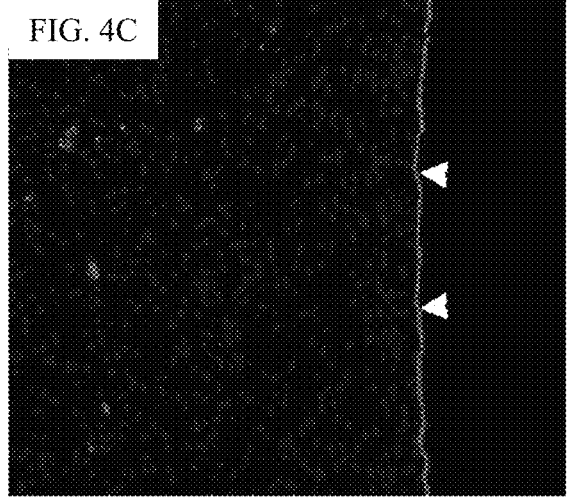
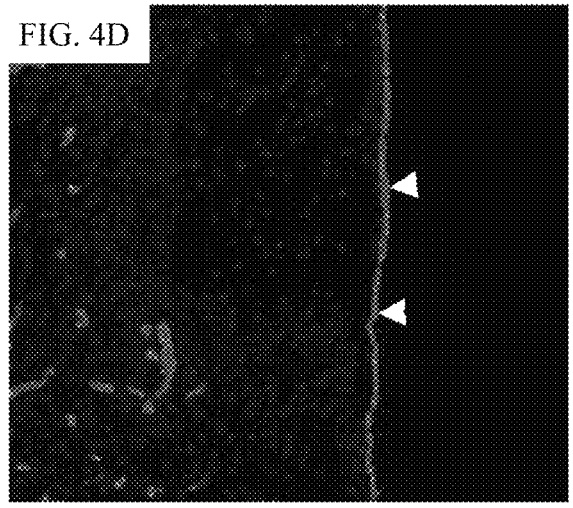

Luminal cell morphology four weeks post-surgery

METHODS OF PREPARING PERSONALIZED BLOOD VESSELS

CROSS-REFERENCE TO RELATED PATENT APPLICATIONS

This application is a Continuation of U.S. application Ser. No. 16/529,973, filed Aug. 2, 2019, which claims the benefit of U.S. Provisional Application No. 62/714,200, filed Aug. 3, 2018.

FIELD OF DISCLOSURE

The present disclosure relates to personalized blood vessels and methods of preparing personalized blood vessels. In various embodiments the personalized blood vessels produced by the methods contemplated herein may be useful in transplantation with improved host compatibility, tissue integration and reduced susceptibility to thrombosis.

BACKGROUND

Vascular diseases constitute a serious and constantly growing health issue on a global scale. The options for replacement of damaged blood vessels are limited today. Autologous transplantation requires suitable vessel in the patient and leads to donor site morbidity. Synthetic vessel replacements are available, but these lack biological integration in the host tissue and long-term patency. There is a need for fully-biological patient-individualized grafts.

International publication number WO/2013/136184 discloses "methods for recellurization of blood vessels;" for example "for producing an allogeneic vein, wherein a donor vein is decellularized and then recellularized using whole blood or bone marrow stem cells."

International publication number WO/2015/181245 discloses "methods for recellularization of valves in valve-bearing veins;" for example "for producing an allogeneic venous valve, wherein a donor valve-bearing vein is decellularized and then recellularized using whole blood or bone marrow stem cells."

SUMMARY OF THE DISCLOSURE

One aspect of the present disclosure relates to a method of preparing a personalized blood vessel comprising, contacting a surface of an acellular tubular scaffold with an undiluted whole blood sample from a subject in need of the personalized blood vessel, wherein the contacting is performed for more than 2 days.

Another aspect of the present disclosure relates to a method of preparing a personalized blood vessel, comprising contacting a surface of an acellular tubular scaffold with a suspension comprising a whole blood sample from a subject in need of the personalize blood vessel, wherein the whole blood sample is diluted in a physiological solution. In some embodiments, the physiological solution maintains colloid oncotic pressure of the extracellular environment, buffers the pH in a $CO_2$ independent matter, and/or provides a cell protective or antioxidant effect.

In some embodiments, a population of cells present in the whole blood sample populates the scaffold.

In some embodiments, the whole blood sample comprises one or more non-cellular factors, wherein one or more non-cellular factors of the whole blood populate the scaffold, and wherein the one or more non-cellular factors promote cellularization of the acellular tubular scaffold and host compatibility of the vessel upon grafting.

In some embodiments, the undiluted whole blood sample or the suspension comprising the whole blood sample further comprises an anti-thrombotic factor.

In some embodiments, the anti-thrombotic factor comprises an anticoagulant agent.

In some embodiments, the anticoagulant agent comprises heparin or a dextran.

In some embodiments, the heparin is present in the undiluted whole blood sample or the suspension comprising the whole blood sample at a concentration from about 0.5 IU/mL to about 150 IU/mL at the beginning of contacting the surface of the acellular tubular scaffold.

In some embodiments, the heparin is present in the undiluted whole blood sample or the suspension comprising the whole blood sample at a concentration of about 6.7 IU/mL at the beginning of contacting the surface of the acellular tubular scaffold.

In some embodiments, the dextran is dextran-40.

In some embodiments, the dextran is present in the undiluted whole blood sample or the suspension comprising the whole blood sample at a concentration from about 1 g/L to about 55 g/L at the beginning of contacting the surface of the acellular tubular scaffold.

In some embodiments, the anti-thrombotic agent comprises ascorbic acid.

In some embodiments, the ascorbic acid is present in the undiluted whole blood sample or the suspension comprising the whole blood sample at a concentration from about 0.2 µg/mL to about 200 µg/mL at the beginning of contacting the surface of the acellular tubular scaffold.

In some embodiments, the concentration of ascorbic acid is present in the undiluted whole blood sample or the suspension comprising the whole blood sample at a concentration of about 5 µg/mL at the beginning of contacting the surface of the acellular tubular scaffold.

In some embodiments, the anti-thrombotic factor comprises acetylsalicylic acid.

In some embodiments, the acetylsalicylic acid is present in the undiluted whole blood sample or the suspension comprising the whole blood sample at a concentration of from about 0.2 µg/mL to about 200 µg/mL at the beginning of contacting the surface of the acellular tubular scaffold.

In some embodiments, the acetylsalicylic acid is present in the undiluted whole blood sample or the suspension comprising the whole blood sample at a concentration of about 5 µg/mL at the beginning of contacting the surface of the acellular tubular scaffold.

In some embodiments, the whole blood sample or the suspension comprising the whole blood blood sample or the suspension comprising the sample further comprises equal to or more than the population average physiological level of a growth factor selected from the group consisting of: granulocyte macrophage-colony stimulating factor (GM-CSF), interleukin (IL)-3, IL-4, neutrophin (NT)-6, pleiotrophin (HB-GAM), midkine (MK), interferon inducible protein-10 (IP-10), platelet factor (PF)-4, monocyte chemotactic protein-1 (MCP-1), RANTES (CCL-5, chemokine (C—C motif) ligand 5), IL-8, IGFs, fibroblast growth factor (FGF)-1, FGF-2, FGF-3, FGF-4, FGF-5, FGF-6, FGF-7, FGF-8, FGF-9, transforming growth factor (TGF)-β, VEGF, platelet-derived growth factor (PDGF)-A, PDGF-B, HB-EGF, hepatocyte growth factor (HGF), tumor necrosis factor (TNF)-α, insulin-like growth factor (IGF)-1, and any combination(s) thereof.

In some embodiments, the growth factor is a fibroblast growth factor (FGF)-2.

In some embodiments, the FGF-2 is human FGF-2.

In some embodiments, the FGF-2 is present in the undiluted whole blood sample or the suspension comprising the whole blood sample at a concentration from about 0.5 ng/mL to about 200 ng/mL at the beginning of contacting the surface of the acellular tubular scaffold.

In some embodiments, the concentration of the FGF-2 is present in the undiluted whole blood sample or the suspension comprising the whole blood sample at a concentration of about 10 ng/mL at the beginning of contacting the surface of the acellular tubular scaffold.

In some embodiments, the growth factor is a vascular endothelial growth factor (VEGF).

In some embodiments, the VEGF is human VEGF.

In some embodiments, the VEGF is present in the undiluted whole blood sample or the suspension comprising the whole blood sample at a concentration from about 4 ng/mL to about 800 ng/mL at the beginning of contacting the surface of the acellular tubular scaffold.

In some embodiments, the VEGF is present in the undiluted whole blood sample or the suspension comprising the whole blood sample at a concentration of about 80 ng/mL at the beginning of contacting the surface of the acellular tubular scaffold.

In some embodiments, the whole blood sample or the suspension comprising the whole blood sample further comprises human serum albumin, wherein the concentration of human serum albumin at the beginning of contacting the surface of the acellular tubular scaffold is about 55 g/L to about 105 g/L.

In some embodiments, the physiological solution comprises an inorganic salt, and a buffer system.

In some embodiments, the buffer system comprises a CO2-independent buffer system In some embodiments, the CO2-independent buffer system comprises a phosphate buffer system.

In some embodiments, the physiological solution exhibits an osmotic pressure substantially similar to whole blood, which preferably is from about 270 mOsm/kg $H_2O$ to about 310 mOsm/kg $H_2O$.

In some embodiments, the physiological solution further comprises an oncotic factor and/or a nutrient.

In some embodiments, the oncotic factor comprises serum albumin.

In some embodiments, the concentration of human serum albumin VEGF is present in the undiluted whole blood sample or the suspension comprising the whole blood sample at a concentration from about 55 g/L to about 105 g/L at the beginning of contacting the surface of the acellular tubular scaffold.

In some embodiments, the nutrient comprises one or more of a sugar, an amino acid, or a vitamin.

In some embodiments, the sugar is D-glucose.

In some embodiments, the physiological solution comprises a growth factor, and antithrombotic factor, a nutrient, and an oncotic factor; wherein the growth factor comprises human FGF-2 and human VEGF; wherein the anti-thrombotic factor comprises one or more of acetylsalicylic acid, heparin or dextran; and wherein the nutrient comprises D-glucose.

In some embodiments, the method does not require contacting the acellular tubular scaffold with a cell culture medium after contacting with whole blood for preparing the personalized blood vessel.

In some embodiments, contacting the surface of the acellular tubular scaffold is for more than 3 days, more than 4 days, more than 5 days, more than 6 days, more than 7 days, for 2 to 21 days, for 3 to 21 days, for 4 to 21 days, for 5 to 21 days, for 6 to 21 days, for 7 to 21 days, or for 7-9 days.

In some embodiments, wherein the acellular tubular scaffold is contacted with the suspension comprising the whole blood sample, and the method further comprises monitoring a plurality of environmental parameters and/or a concentration of a nutrient during the preparation of the personalized blood vessel.

In some embodiments, the methods of the present disclosure further comprise adjusting the plurality of environmental parameters.

In some embodiments, the plurality of environmental parameters comprises temperature, pH, oxygen, and/or $CO_2$.

In some embodiments, the acellular tubular scaffold is contacted with the suspension comprising the whole blood sample, and the method further comprises monitoring a concentration of a nutrient in the suspension.

In some embodiments, the methods of the present disclosure further comprise continuously or regularly adjusting the concentration of the nutrient.

In some embodiments, the nutrient is D-glucose, and wherein the D-Glucose concentration is adjusted continuously or regularly to maintain the D-glucose concentration at about 3 to about 11 mmol/L.

In some embodiments, the concentration of D-glucose in the suspension is monitored by measuring the concentration of D-glucose in a sample collected from the suspension.

In some embodiments, the concentration of D-glucose in the suspension is measured once every day.

In some embodiments, the concentration of D-glucose in the suspension is monitored by measuring the concentration of D-glucose using a sensor that is in contact with the suspension.

In some embodiments, the sensor is continuously in contact with the suspension during the contacting.

In some embodiments, D-glucose is added when the measured concentration of D-glucose in the suspension is below 4 mmol/L.

In some embodiments, D-glucose is added to reach a final concentration of 10 mmol/L of D-glucose in the suspension.

In some embodiments, the surface of the acellular tubular scaffold is the inner surface of the acellular tubular scaffold.

In some embodiments, the whole blood comprises peripheral blood or umbilical cord blood.

In some embodiments, the method further comprises monitoring a concentration of human serum albumin, wherein the concentration of human serum albumin is about 55 g/L to about 105 g/L at the beginning of contacting the surface of the acellular tubular scaffold.

In some embodiments, wherein contacting the acellular tubular scaffold results in proliferation and/or differentiation of a plurality of progenitor cells to a plurality of endothelial cells.

In some embodiments, the plurality endothelial cells express VE-cadherin, AcLDL, vWF, and/or CD31.

In some embodiments, the acellular tubular scaffold is a decellularized blood vessel.

In some embodiments, the acellular tubular scaffold is continuously perfused with the suspension or whole blood.

In some embodiments, the acellular tubular scaffold is perfused at a speed of about 0.1 mL to about 50 mL per minute.

In some embodiments, the acellular tubular scaffold is perfused at a speed of about 2 mL per minute.

In some embodiments, the scaffold is perfused with a closed recirculation of the suspension or whole blood.

In some embodiments, the continuous contacting is perfusion conducted using a bioreactor.

In some embodiments, the contacting is conducted in vitro.

In some embodiments, the contacting is conducted at about 8° C. to about 40° C.

In some embodiments, wherein the contacting is conducted at about 20° C. to about 25° C.

In some embodiments, the personalized blood vessel is a vein.

In some embodiments, the vein is a femoral vein.

In some embodiments, the methods of the present disclosure further comprise assessing the venous valve function of the personalized blood vessel using a valve competence test.

Another aspect of the present disclosure relates to a personalized blood vessel prepared by the method of any one of the methods of preparing a personalized blood vessel disclosed herein.

In some embodiments, the personalized blood vessel has been implanted into a subject by surgery.

Another aspect of the present disclosure relates to a method of surgery comprising implanting the personalized blood vessel disclosed herein into a subject in need thereof.

Another aspect of the present disclosure relates to a personalized blood vessel for use in a method of surgery, wherein the method comprises implanting the personalized blood vessel of disclosed herein into a subject in need thereof.

In some embodiments, the subject is human.

Another aspect of the present disclosure relates to a bioreactor for preparing a personalized blood vessel, the bioreactor comprising a peristaltic pump, a container comprising a sampling port, a first connector, and a second connector, wherein the first and second connectors are directly or indirectly connected to the container, wherein each connector is connected to an end of a tubular scaffold for preparing a personalized blood vessel prepared by the methods disclosed herein, wherein when the first and second connectors are connected to the two ends of a tubular scaffold, the peristaltic pump mediates the circulation of a suspension or solution in a closed circuit.

In some embodiments, the first and second connectors are Luer connectors.

In some embodiments, the sampling port is an injection port.

In some embodiments, the bioreactor further comprises an injection port.

In some embodiments, the injection port is connected to a reservoir of D-glucose.

In some embodiments, the first container is directly connected to the container by a tube, and/or the second container is directly connected to the container by a tube.

In some embodiments, the bioreactor comprises one or more sample ports.

In some embodiments, the bioreactor further comprises one or more sensors for measuring glucose level.

In some embodiments, the bioreactor further comprises a pH adjusting module.

In some embodiments, the bioreactor further comprises a $CO_2$ adjusting module.

Another aspect of the present disclosure relates to a method of preparing a personalized blood vessel, the method comprising contacting a surface of an acellular tubular scaffold with a component contained in the whole blood, which is enriched or selected prior to use in contacting the surface.

In some embodiments, the component is selected from thrombocytes, nucleated cells, proteins, growth factors, signaling factors, immunoglobulins, and any combinations thereof.

In some embodiments, the component is enriched by centrifugation, gradient centrifugation;
or selected by selective adhesion, filtration, or sorting.

In some embodiments, the surface is an inner surface of the acellular tubular scaffold.

BRIEF DESCRIPTION OF THE DRAWINGS

FIGS. 1A-1B are angiograms of a sham operated vena cava (FIG. 1A) and a transplanted P-TEV (FIG. 1B). Metal clips are indicated by arrow heads to localize the anastomoses.

FIGS. 3A-3D are a series of immunohistograms showing DAPI staining and CD31 immunostaining of vena cava two weeks post-surgery. FIG. 3A shows native vena cava proximal to the anastomoses. FIGS. 3B-3D show proximal (FIG. 3B), center (FIG. 3C), and distal (FIG. 3D) parts of the P-TEV. Arrow heads indicate CD31-positive cells.

FIGS. 4A-4D depict images showing Vena cava cellularization four weeks post surgery. FIGS. 4A-4D are a series of immunohistograms showing DAPI staining and CD31 immunostaining of vena cava 4-5 weeks post-surgery. FIG. 4A shows native vena cava proximal to the anastomoses. FIGS. 4B-4D show proximal (FIG. 4B), center (FIG. 4C), and distal (FIG. 4D) parts of the P-TEV. Arrow heads indicate CD31-positive cells.

FIGS. 5A-5B is a series of images at 40× magnification showing H&E staining of native vena cava (FIG. 5A) and P-TEV transplant (FIG. 5B) 4-5 weeks post-surgery. Arrows indicate endothelial cells in the native tissue and cells with plated endothelial cell-like morphology in the P-TEV transplant.

DETAILED DESCRIPTION OF THE DISCLOSURE

Figures 2A, 2B:
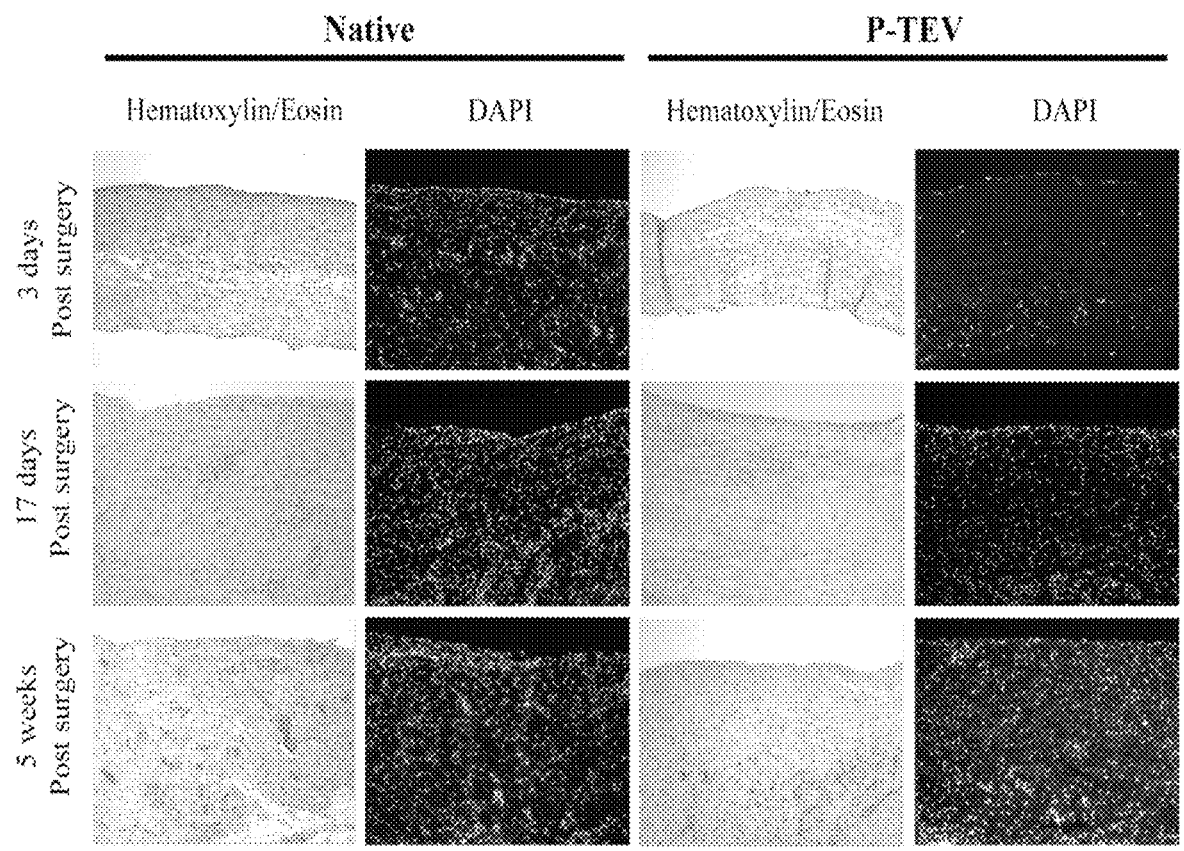
FIGS. 2A-2B are a series of images showing Hematoxylin and Eosin (H&E) staining and 4',6-diamidino-2-phenylindole (DAPI) staining of native vena cava ("Native," FIG. 2A) and P-TEV transplants ("P-TEV," FIG. 2B) from adjacent sections 3 days, 2 weeks, 17 days, and 4-5 weeks post-surgery.

The instant disclosure is based, inter alia, upon the discovery that cells and non-cellular factors in the blood were able to condition acellular tubular scaffolds (e.g., a decellularized blood vessel or a bioprinted tubular scaffold) to produce personalized blood vessels. The instant disclosure further provides, inter alia, contacting acellular tubular scaffolds with either undiluted whole blood samples or a suspension comprising a whole blood sample diluted in a physiological solution in an in vitro process produces personalized blood vessels with improved host compatibility and reduced susceptibility to thrombosis.

Accordingly, one aspect of the present disclosure relates to a method of preparing a personalized blood vessel comprising, contacting a surface of an acellular tubular scaffold with an undiluted whole blood sample from a subject in need of the personalized blood vessel, wherein the contacting is performed for more than 2 days.

Another aspect of the present disclosure relates to a method of preparing a personalized blood vessel, comprising contacting a surface of an acellular tubular scaffold with a suspension comprising a whole blood sample from a subject in need of the personalize blood vessel, wherein the whole blood sample is diluted in a physiological solution. In some embodiments, the surface of the acellular tubular scaffold is the inner surface of the acellular tubular scaffold.

As used herein, the term "personalized blood vessel" refers to a tubular structure capable of carrying blood through a tissue or organ that is not a native blood vessel. The tubular structure can be prepared by decellularizing a native blood vessel from a donor, thereby obtaining an acellular scaffold, and reconditioned/recellularizing the scaffold using cells from another individual. An acellular scaffold can also be obtained by assembling a biocompatible material in vitro (e.g., bioprinting or polymer self-assembly). As used herein, the terms "recondition," "reconditioning," and "reconditioned" are used to describe the modification of the acellular scaffold by components of the recellularization/recondition (RC) solution containing whole blood. As used herein, the terms "recellularize," "recellularizing," and "recellularization" are used in either context, and do not require that the initial starting material has cells attached. A personalized blood vessel can be a personalized vein, artery, or capillary. In certain embodiments, a personalized blood vessel is useful to replace a native blood vessel.

Preparation of the Acellular Tubular Scaffold from Donor

The method of preparing a personalized blood vessel as disclosed herein employs an acellular tubular scaffold. As used herein, the term "acellular tubular scaffold" refers to a tubular scaffold that is substantially cell-free. An acellular tubular scaffold can be prepared by decellularizing a native blood vessel from a donor. The donor can be a human or an animal from a suitable species. An acellular scaffold can also be obtained by assembling a biocompatible material in vitro (e.g., bioprinting or polymer self-assembly).

The acellular tubular scaffold can be prepared by any method known in the art, for example, decellularization of a native blood vessel. The native blood vessel can be of human origin or can be obtained from suitable animal species. A tubular structure can be prepared by tissue-culture methods from biocompatible scaffold and cells in vitro and can serve as the starting material for the preparation of an acellular scaffold. In certain embodiments, the acellular tubular scaffold is obtained by a method of decellularization disclosed herein. In certain embodiments, the method of preparing a personalized blood vessel disclosed herein further comprises decellularizing a native blood vessel, thereby obtaining an acellular tubular scaffold.

As used herein, the term "decellularize," "decellularized," "decellularizing," or "decellularization" refers to the process of removing cells from a blood vessel (including any venous valve in the blood vessel). Effective decellularization is dictated by factors such as tissue density and organization, geometric and biologic properties desired for the end product, and the targeted clinical application. Decellularization of blood vessels with preservation of the ECM integrity and bioactivity can be optimized by those skilled in the art, e.g., by choosing specific agents and techniques during processing.

Successful decellularization is defined as the absence cells, such as endothelial cells, smooth muscle cells, and nuclei in histologic sections using standard histological staining procedures. While most cell removal agents and methods may alter ECM composition and cause some degree of ultrastructure disruption, minimization of these undesirable effects is desired. Methods of decellularization are known in the art, e.g., in U.S. Patent Publication No. 2017/0071738.

Accordingly, in certain embodiments, the decellularization process removes all nuclei, as detected by a method known in the art (e.g., DAPI staining, DNA quantification). In certain embodiments, the decellularization process reduces or removes HLA class-I antigens and HLA class-II antigens, as detected by a method known in the art (e.g., immuohistochemical assays for HLA class-I and class-II antigens).

In certain embodiments, the ECM components are substantially retained in the decellularization process. During and following the process of decellularization, the morphology and architecture of the ECM can be examined visually and/or histologically to verify that the decellularization process has not compromised the three-dimensional structure and bioactivity of the ECM scaffold. Histological analysis by staining (e.g., H&E staining, Masson's Trichrome staining, or Verhoeff-Van Gieson staining) may be useful to visualize decellularized blood vessel architecture and preservation of ECM components, such as collagen I, collagen IV, laminin and fibronectin. Other methods known in the art may be used for determining the preservation of ECM components, such as glycosaminoglycans and collagen.

One or more cellular disruption solutions may be used to decellularize a blood vessel. A cellular disruption solution generally includes at least one detergent, such as SDS, PEG, or Triton X. A particularly preferred detergent is Triton X (e.g., Triton X-100). A cellular disruption solution may comprise an organic solvent, e.g., Tri-n-Butyl Phosphate (TNBP). A cellular disruption solution can also have a substantially lower osmotic pressure than blood, thereby facilitating cell lysis. Alternatively, a cellular disruption solution can be isotonic. Cellular disruption solution also can include enzymes such as, without limitation, one or more nucleases (e.g., DNases or RNases) and proteinases (e.g., collagenases, dispases, or trypsin). A cellular disruption solution that comprises DNase I may also include calcium chloride and magnesium chloride (A12858, Life Technologies) to activate the enzyme. In certain embodiments, a cellular disruption solution further comprises one or more protease inhibitors (e.g., phenyl methyl sulfonyl fluoride (PMSF), collagenase inhibitors). In certain embodiments, a cellular disruption solution may further include an antibiotic (e.g., penicillin, streptomycin, or amphotericin) or ethylenediaminetetraacetic acid (EDTA).

In certain embodiments, perfusion methods may be used to treat the blood vessel (e.g., valve-bearing vein) with cellular disruption solutions for decellularization of the blood vessel. Alternating the direction of perfusion (e.g., antegrade and retrograde) can help to effectively decellularize a valve-bearing veins. Decellularization as described herein essentially removes the cells lining the valve-bearing veins from the inside out, resulting in very little damage to the ECM. Depending upon the size and weight of the blood vessel and the particular detergent(s) and concentration of detergent(s) in the cellular disruption solution, a valve-bearing vein is generally perfused between 4 and 48 hours; or between 8 and 24 hours with cellular disruption medium. Including washes, a blood vessel may be perfused for up to about 48 hours or 24 hours for Triton X, about 8 hours for TNBP, about 16 hours for DNase, about 1 hour total washes and about 48 hours final wash. In some embodiments the aforementioned profusion procedure is repeated for 1-14 cycles; 1-5 cycles; 2-4 cycles; 1-3 cycles; or 2 cycles; or 3 cycles; or 4 cycles; or 5 cycles; or 6 cycles. In certain embodiments, the decellularization is performed by perfusion with the aforementioned reagents continuously for 100 hours, 110 hours, 120 hours, 130 hours, 140 hours, 150 hours, 160 hours, 170 hours, 180 hours, 190 hours, 200 hours, 210 hours, 220 hours, 230 hours, 240 hours, 250 hours, 260 hours, 270 hours, 280 hours, 290 hours, 300 hours, 310 hours, 320 hours, 330 hours, 340 hours, 350 hours, or more. Perfusion generally is adjusted to physiologic conditions including pulsatile flow, rate and pressure. Perfusion decellularization as described herein can in some embodiments be compared to immersion decellularization as described, for example, in U.S. Pat. Nos. 6,753,181 and 6,376,244. In certain embodiments, the decellularization is conducted according to the method of decellularizing a blood vessel as provided in Example 1 infra.

In certain embodiments, the acellular tubular scaffold is a synthesized and/or assembled scaffold, e.g., a scaffold obtained by assembling a biocompatible material in vitro. Methods of preparing such scaffold, e.g., bioprinting or polymer self-assembly, are known in the art, and non-limiting examples are provided in U.S. Patent Publication Nos. 2017/0304503 and 2016/0354194.

Accordingly, in certain embodiments, the method disclosed herein further comprises a step of preparing a bioprinted tubular blood vessel scaffold using a bioprinted polymeric scaffold. The bioprinted blood vessel scaffold is prepared on a polymer (natural or synthetic), which may be in a gel form, sponge form, foam form, patch form, or a semi-liquid/fluid form. In certain embodiments, a bioprinted scaffold is perfused with whole blood or whole blood diluted in a solution, e.g., a suspension, which includes whole blood.

In certain embodiments, the ECM components may be added to the polymer in a powder form. In the present disclosure the powder for preparing the composition of the present disclosure is prepared by treating a tissue with a chemical, freeze-drying the chemical treated tissue, and homogenization of freeze-dried tissue. In certain embodiments, the powder is filamentous.

In certain embodiments, bioprinted polymeric scaffold may include gelatin and fibrin. The gelatin and fibrin may form an interpenetrating polymer network that mimics natural ECM and may be optimized for cell attachment, bioprinting, transparency, and biocompatibility.

In certain embodiments, components of the ECM are or may be isolated and/or purified from a tissue of a mammal (e.g., a pig, a cow, a lamb, a goat, a sheep, a chimpanzee, a monkey, a human, or other primate) or generated using recombinant DNA technology involving gene or gene fragments of a mammal (e.g., a pig, a cow, a lamb, a goat, a sheep, a chimpanzee, a monkey, a human, or other primate) encoding the respective ECM component (e.g., collagens, elastins, laminins, glycosaminoglycans, proteoglycans, antimicrobials, chemoattractants, cytokines, and growth factors) and expressed in from a suitable expression system (prokaryotic or eukaryotic (e.g., yeast, insect, or mammalian cells)), and subsequently isolated and/or purified by suitable method in the art. In certain embodiments, one or more of the ECM components may be added to the polymeric scaffold for preparing a bioprinted polymeric scaffold, and then the scaffold is perfused with whole blood or whole blood diluted in a solution, e.g., a suspension, which includes whole blood, for preparing a personalized blood vessel.

In some embodiments, the tubular scaffold may be prepared by methods such as 3D-printing of different materials, self-assembly, chemical or biochemical manufacturing. In some embodiments, the tubular scaffold is manufactured from biological and non-biological starting material.

Patient Whole Blood

In some embodiments, a population of cells present in the whole blood sample populates the scaffold. The patient whole blood may be used undiluted or diluted with a physiological perfusion solution such as described in the examples 4-5 or other organ preservative solutions such as for example Perfadex™, STEEN™, Euro Collins solution, University of Wisconsin cold storage solution or Celsior® solution.

In certain embodiments, the whole blood comprises peripheral blood (e.g., peripheral venous blood). In certain embodiments, the whole blood is peripheral blood (e.g., peripheral venous blood). In certain embodiments, the whole blood comprises umbilical cord blood. In certain embodiments, the whole blood is umbilical cord blood.

The terms "patient" and "subject" are used interchangeably in this disclosure and refer to a human or non-human animal (e.g., a mammal). Non-limiting examples include humans, bovines, rats, mice, dogs, cats, monkeys, goat, sheep, cows, and deer. In some embodiments, the subject is a human.

Undiluted Patient Whole Blood

One aspect of the present disclosure relates to a method of preparing a personalized blood vessel comprising, contacting a surface of an acellular tubular scaffold with an undiluted whole blood sample from a subject in need of the personalized blood vessel, wherein the contacting is performed for more than 2 days.

In certain embodiments, the cells and/or progenitor cells present in the blood populate the scaffold. In some embodiments, a population of cells present in the whole blood sample populates the scaffold. The term "whole blood" refers to blood drawn from a body, organ, or tissue, from which none of the components has been removed.

The skilled person would appreciate that during the collection of whole blood, a small volume of an anti-thrombotic agent may be added during or immediately after the blood sample is drawn from a subject. Where the volume of the anti-thrombotic agent does not exceed about 5% or at least not 10% of the volume of the blood with which the anti-thrombotic agent is mixed, the whole blood thereby prepared is considered undiluted. Similarly, in certain embodiments, the whole blood may be supplemented with one or more other agents (e.g., anti-thrombotic agents, nutrients, diluent, preservatives, and $CO_2$-independent buffer system), wherein the total volume of the added substance(s)—not including any anti-thrombotic agent initially introduced at the time of collection—does not exceed about 5% or at least not about 10% of the volume of the whole blood, the supplemented whole blood is considered undiluted.

In certain embodiments, the method does not require contacting the acellular tubular scaffold with a cell culture medium for preparing the personalized blood vessel. In certain embodiments, the whole blood is used in the method disclosed herein within about 1 hour, about 2 hours, about 4 hours, about 6 hours, about 8 hours, about 12 hours, about 24 hours, about 36 hours, about 2 days, about 3 days, or about 1 week after the collection of the whole blood. In certain embodiments, the whole blood is stored at about 2° C. to about 8° C. before use in the method.

Diluted Patient Whole Blood

In another aspect, the present invention relates to contacting the acellular tubular scaffold with diluted patient whole blood.

The patient whole blood is considered diluted if the whole blood drawn from the patient is diluted with any type of solution, buffer, or aqueous liquid at least 15%, 20%, 30%, 40%, 50%, 60%, 70%, 80%, 90%, 100%, 110%, 120%, 130%, 140%, 150%, 160%, 170%, 180%, 190%, or 200%. In some embodiments, the whole blood sample is diluted 1:1, i.e. 1 volume of whole blood is mixed with 1 volume diluent. In some embodiment, the whole blood sample may be diluted 1:2, 1:3, 1:4, 1:5, 1:6, 1:7, 1:8, 1:9, or 1:10.

In certain embodiments, the whole blood is diluted in a physiological solution. In certain embodiments, the diluent is a physiological solution containing additional oncotic and other factors as described in the examples x-y or other organ preservative solutions such as for example Perfadex™ (see Ex. 5 below), STEEN™ (non-toxic physiological salt solution comprising human serum albumin and dextran 40, or a solution as described in U.S. Pat. No. 8,980,541) Euro Collins solution (see Ex. 5 below), University of Wisconsin cold storage solution (see Ex. 5 below) or Celsior® solution (see Ex. 5 below). In certain embodiments, the physiological solution is STEEN™ solution.

In some embodiments, the oncotic factors contemplated to be use to regulate the osmotic pressure of the physiological solution comprise serum albumin, globulin, or fibrinogen. In some embodiments, the oncotic factor comprises serum albumin. In some embodiments, gelatin may be used to regulate the oncotic pressure of the solution.

A physiological solution may further comprise one or more nutrients (e.g., amino acid, monosaccharide (e.g., D-glucose), vitamin, inorganic ion, trace element, and/or salt) and/or growth factors, e.g., at physiological concentrations, to support survival, proliferation, and/or differentiation of cells. In some embodiments, the nutrient comprises one or more of a sugar, an amino acid, or a vitamin. In some embodiments, the sugar is D-glucose.

In some embodiments, the physiological solution comprises an inorganic salt, and a buffer system. In some embodiments, the buffer system comprises a $CO_2$-independent buffer system. In some embodiments, the $CO_2$-independent buffer system comprises a phosphate buffer system. The physiological solution may contain any of the further agents to be added to the whole blood or diluted whole blood as described below.

Further Agents Added to Whole Blood or Diluted Whole Blood Samples

In some embodiments, further agents described herein are added to the whole blood sample or to the suspension of whole blood or the diluted whole blood sample before or during contacting the acellular tubular scaffold with the whole blood. As explained above, as long as the addition of the factors described herein does not dilute the whole blood with more than 5 or at least not more than 10%, the whole blood sample is still considered undiluted. If the whole blood sample is diluted more than 15% with the factors described herein, then the whole blood sample is diluted.

In certain embodiments, the suspension with whole blood or diluted whole blood or the undiluted whole blood further comprises an anti-thrombotic agent. In certain embodiments, an anti-thrombotic agent is or has been introduced to the whole blood before contacting the acellular tubular scaffold. In certain embodiments, the anti-thrombotic agent comprises an anticoagulant agent. In certain embodiments, the anticoagulant agent comprises heparin, a dextran, In certain embodiments the anti-thrombotic agent comprises a platelet-inhibitor such as ascorbic acid.

In certain embodiments, the anticoagulant agent comprises heparin. Effective concentrations of heparin for preventing coagulation are known in the art. In some embodiments, the heparin is present in the undiluted whole blood sample or the suspension comprising the whole blood sample at a concentration from about 0.5 IU/mL to about 150 IU/mL at the beginning of contacting the surface of the acellular tubular scaffold. In certain embodiments, the concentration of heparin at the beginning of the contacting is about 5 to about 50 IU/ml. In certain embodiments, the concentration of heparin at the beginning of the contacting is about 5, about 6, about 7, about 8, about 9, about 10, about 15, or about 20 IU/mL. In certain embodiments, the concentration of heparin at the beginning of the contacting is about 6.7 IU/ml. In some embodiments the bioreactor with tubing and vein is preflushed with a 50 IU/ml heparin in PBS solution (for example for 1 hour), then emptied and filled with blood solution; and in various embodiments, a 1:10 dilution is obtained by the switching of solutions resulting in around 5 IU/ml heparin in the blood solution. In certain embodiments vacutainers containing 17 IU heparin/mL whole blood are used resulting in about 8.5 IU heparin in the blood solution.

In certain embodiments, the anticoagulant agent comprises a dextran. Dextran of any average molecular weight can be used. In certain embodiments, the dextran has an average molecular weight of about 40 kD, i.e., the dextran is dextran-40. In certain embodiments, the dextran has an average molecular weight of about 60 kD, i.e., the dextran is dextran-60. In certain embodiments, the dextran has an average molecular weight of about 70 kD, i.e., the dextran is dextran-70. In certain embodiments, the concentration of the dextran at the beginning of the contacting is about 1 to about 55 g/L. In certain embodiments, the concentration of the dextran at the beginning of the contacting is about 1, about 2, about 3, about 4, about 4.5, about 5, about 10, or about 20 g/L. In certain embodiments, the concentration of the dextran at the beginning of the contacting is about 5 g/L.

In certain embodiments, the anti-thrombotic agent comprises ascorbic acid. In certain embodiments, the concentration of ascorbic acid at the beginning of the contacting is about 0.2 to about 200 µg/ml. In certain embodiments, the concentration of ascorbic acid at the beginning of the contacting is about 1, about 5, about 10, about 20, about 50, or about 100 µg/mL. In certain embodiments, the concentration of ascorbic acid at the beginning of the contacting is about 5 µg/mL.

Two or more anti-thrombotic agents (e.g., anticoagulant agents) can be combined in the present invention. In certain embodiments, the suspension comprises two or more of the agents selected from the group consisting of heparin, dextran (e.g., dextran-40), and ascorbic acid. In certain embodiments, the suspension comprises heparin, dextran (e.g., dextran-40), and ascorbic acid. The skilled person would appreciate that when two or more anti-thrombotic agents are combined, at least one of them may be used at a lower concentration than the concentration at which it would be used alone. In certain embodiments, the suspension comprises about 6.7 IU/mL of heparin, about 6.7 mg/mL of dextran-40, and about 4.5 µg/mL of ascorbic acid. In certain embodiments, the suspension comprised at least about 6.7 IU/mL of heparin, about 6.7 mg/mL of dextran-40, and about 4.5 µg/mL of ascorbic acid.

In certain embodiments, the suspension with whole blood or diluted whole blood or the undiluted whole blood further comprises a growth factor selected from the group consisting of: granulocyte macrophage-colony stimulating factor (GM-CSF), interleukin (IL)-3, IL-4, neutrophin (NT)-6, pleiotrophin (HB-GAM), midkine (MK), interferon inducible protein-10 (IP-10), platelet factor (PF)-4, monocyte chemotactic protein-1 (MCP-1), RANTES (CCL-5, chemokine (C—C motif) ligand 5), IL-8, IGFs, fibroblast growth factor (FGF)-1, FGF-2, FGF-3, FGF-4, FGF-5, FGF-6, FGF-7, FGF-8, FGF-9, transforming growth factor (TGF)-β, VEGF, platelet-derived growth factor (PDGF)-A, PDGF-B, HB-EGF, hepatocyte growth factor (HGF), tumor necrosis factor (TNF)-α, insulin-like growth factor (IGF)-1, and any combination(s) thereof. In certain embodiments, the growth factor is a human growth factor. In certain embodiments, the concentration of the growth factor is equal to the population average physiological level of the growth factor. In certain embodiments, the concentration of the growth factor is more than the population average physiological level of the growth factor. In certain embodiments, the growth factor is supplemented as a recombinant protein.

In certain embodiments, the growth factor is a fibroblast growth factor (FGF)-2. In certain embodiments, the FGF-2 is human FGF-2. In certain embodiments, the concentration of the FGF-2 at the beginning of the contacting is about 0.5 to about 200 ng/ml. In certain embodiments, the concentration of the FGF-2 at the beginning of the contacting is about 10 ng/ml. In certain embodiments, the FGF-2 is supplemented prior to the contacting at the concentration of about 0.5 to about 200 ng/ml (e.g., about 10 ng/ml). In certain embodiments, the FGF-2 is recombinant human FGF-2 (rhFGF-2). In certain embodiments, the concentration of the rhFGF-2 at the beginning of the contacting is about 0.5 to about 200 ng/ml (e.g., about 10 ng/ml).

In certain embodiments, the growth factor is a vascular endothelial growth factor (VEGF). In certain embodiments, the VEGF is human VEGF. In certain embodiments, the concentration of the VEGF at the beginning of the contacting is about 4 to about 800 ng/mL. In certain embodiments, the concentration of the VEGF at the beginning of the contacting is about 80 ng/ml. In certain embodiments, the VEGF is supplemented prior to the contacting at the concentration of about 4 to about 800 ng/mL (e.g., about 80 ng/mL). In certain embodiments, the VEGF is recombinant human VEGF (rhVEGF). In certain embodiments, the concentration of the rhVEGF at the beginning of the contacting is about 4 to about 800 ng/mL (e.g., about 80 ng/mL).

In certain embodiments, the suspension with whole blood or diluted whole blood or the undiluted whole blood further comprises acetylsalicylic acid. In certain embodiments, the concentration of acetylsalicylic acid at the beginning of the contacting is between 0.2 μg/mL and 200 μg/mL; or 0.5 μg/mL and 100 μg/mL; or 0.1 μg/mL and 50 μg/mL; or 1 μg/mL and 25 μg/mL; or 1 μg/mL and 10 μg/mL; or 2 μg/mL and 10 μg/mL; or 3 μg/mL and 8 μg/mL; or 4 μg/mL and 6 μg/mL. In certain embodiments, the concentration of acetylsalicylic acid at the beginning of the contacting is about 0.5 μg/mL; or about 1 μg/mL; or about 2 μg/mL; or about 3 μg/mL; or about 4 μg/mL; or about 5 μg/mL; or about 6 μg/mL; or about 7 μg/mL; or about 8 μg/mL; or about 8 μg/mL; or about 8 μg/mL; or about 9 μg/mL; or about 10 μg/mL; or about 25 μg/mL or about 50 μg/mL; or about 100 μg/mL; or about 200 μg/mL. In certain embodiments, the concentration of acetylsalicylic acid at the beginning of the contacting is about 5 μg/mL. In certain embodiments, VEGF is supplemented prior to the contacting at a concentration between 4 ng/mL and 800 ng/mL; or between 10 ng/mL and 400 ng/mL; or between 20 ng/mL and 200 ng/mL; or between 40 ng/mL and 200 ng/mL; or between 60 ng/mL and 100 ng/mL; or between 70 ng/mL and 90 ng/mL.

In certain embodiments, the concentration of human serum albumin (HSA) at the beginning of the contacting is between 50 mg/mL and 150 mg/mL; or between 50 mg/mL and 125 mg/mL; or between 50 mg/mL and 100 mg/mL; or between 60 mg/mL and 90 mg/mL; or between 60 mg/mL and 80 mg/mL; or between 65 mg/mL and 75 mg/mL. In certain embodiments, the concentration of human serum albumin at the beginning of the contacting is about 55 to about 105 mg/m, which is the amount when whole blood is diluted in a solution by 2-fold. In certain embodiments, the concentration of human serum albumin at the beginning of the contacting is about 45 to about 69 mg/mL. In certain embodiments, the concentration of HSA in a solution is about 70 mg/ml, and the concentration of HSA in human blood is about 45 mg/mL, and the whole blood in diluted in the solution, the HSA in the suspension comprising whole blood is 55-60 mg/mL (i.e., 2-fold dilution of whole blood in the solution). In certain embodiments, the concentration of human serum albumin after whole blood is diluted in a solution comprising 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold diluted HSA.

In certain embodiments, the suspension with whole blood or diluted whole blood or the undiluted whole blood comprises one or more nutrients and/or growth factors, e.g., at physiological concentrations, to support survival, proliferation, and/or differentiation of cells. In certain embodiments, the nutrients are selected from the group consisting of monosaccharides (e.g., D-glucose), amino acids (natural amino acids), vitamins, inorganic ions, trace elements, salts, and any combinations thereof. In certain embodiments, the amino acid included as a nutrient may be one or more of: L-ArginineHCl, L-Cystine2HCl, L-CystineHCl $H_2O$, L-HistidineHCl $H_2O$, L-Isoleucine, L-Leucine, L-LysineHCl, L-Methionine, L-Phenylalanine, L-Threonine, L-Tryptophan, L-Tyrosine2$H_2O$, L-Valine, L-Alanine, L-Asparagine, L-Aspartic acid, L-Glutamic acid, Glycine, L-Proline, L-Serine, and/or L-Hydroxyproline. In certain embodiments, the vitamin included as a nutrient may be one or more of: K—Ca-Pantothenate, Choline Chloride, Folic acid, i-Inositol, Niacinamide, Pyridoxal HCl, Pyridoxine HCl, Riboflavin, Thiamine HCl, Biotin, Vitamin B12, Para-aminobenzoic acid, Niacin, Ascorbic acid, a-Tocopherol phosphate, Calciferol, Menadione, Vitamin A. In certain embodiments, the inorganic ion is included in the form of an inorganic salt including but not limited to $CaCl_2$, KCl, $MgSO_4$, NaCl, $NaHCO_3$, $NaHPO_4$, $KNO_3$, $NaSeO_3$, $Ca(NO_3)_2$, $CuSO_4$, $NaHPO_4$, $MgCl_2$, $Fe(NO_3)_3$, $CuSO_4$, $FeSO_4$, and/or $KH_2PO_4$.

In some embodiments, the suspension with whole blood or diluted whole blood or the undiluted whole blood comprises about 0.7% to about 1.5% salt. In some embodiments, the physiological solution comprises about 0.7%, about 0.8%, about 0.9%, or about 1.0% salt.

In certain embodiments, the suspension comprises a $CO_2$-independent buffer system. In some embodiments, the $CO_2$-independent buffer system comprises a phosphate buffer system. In some embodiments, the $CO_2$-independent buffer system comprises a phosphate buffer and sodium bicarbonate. In certain embodiments, the suspension further comprises one or more of: D-Glucose, Phenol red, HEPES, Sodium pyruvate, Glutathione (reduced), Hypoxantine.Na, Thymidine, Lipoic acid, Putrescine 2HCl, Bacto-peptone, Thymine, Adenine sulphate, Adenosine-5-triphosphate, Cholesterol, 2-deoxy-D-ribose, Adenosine-5-phosphate, Guanine HCl, Ribose, Sodium acetate, Tween 80, Uracil, and/or Xanthine Na.

In certain embodiments, a non-cellular factor of the whole blood suspension promotes cellularization of the acellular tubular scaffold, e.g., by promoting cell survival, proliferation, and/or differentiation. In certain embodiments, the non-cellular factor is a non-cellular component present in the whole blood. In certain embodiments, the non-cellular blood factor is a factor generated from the whole blood (e.g., from the cells in the whole blood) during the contacting. In certain embodiments, the non-cellular blood factor promotes host compatibility, cellularization or integration of the vessel upon grafting. Non-limiting examples of non-cellular factors of the present invention are provided in the following table:

| Non-cellular factors |
| --- |
| Hemoglobin subunit delta |
| Hemoglobin subunit epsilon |
| Plasminogen |
| Hemoglobin subunit alpha |
| Hemoglobin subunit gamma-1 |
| Serum albumin |
| Alpha-2-macroglobulin |
| Complement C1q subcomponent subunit B |
| Hemoglobin subunit beta |
| Thrombospondin-1 |
| Adenylate kinase isoenzyme 1 |
| Fibrinogen alpha chain |
| Flavin reductase (NADPH) |
| Complement C3 |
| von Willebrand factor |
| Fibrinogen beta chain |
| Peroxiredoxin-2 |
| Inter-alpha-trypsin inhibitor heavy chain H2 |
| Hemoglobin subunit alpha |
| Immunoglobulin kappa variable 2-30 |
| Apolipoprotein B-100 |
| Fermitin family member 3 |
| Ceruloplasmin |
| Phosphoinositide phospholipase C |
| Fibrinogen beta chain |
| Isoform 2 of Fermitin family homolog 3 |
| Alpha-2-macroglobulin |
| Isoform 2 of Spectrin alpha chain, erythrocytic 1 |
| Protein S100-A8 |
| Complement C1qB (Fragment) |
| Fibulin-1 |
| Serum paraoxonase/arylesterase 1 |
| Hemopexin |
| Fibrinogen alpha chain |
| Hemoglobin subunit beta |
| Complement C4-B |
| Complement C4-A |
| Isoform Er16 of Ankyrin-1 |
| Catalase |
| Complement C3 |
| GC, vitamin D binding protein |
| Serum albumin |
| Serum albumin |
| Fructose-bisphosphate aldolase A |
| Coagulation factor X protein |
| Inter-alpha-trypsin inhibitor heavy chain H2 |
| Vitamin K-dependent protein S |
| 5-aminoimidazole-4-carboxamide ribonucleotide formyltransferase/IMP cyclohydrolase |
| Profilin |
| Peroxiredoxin 2 |
| Complement component 4A |
| von Willebrand factor |
| Complement component C7 |
| Profilin-1 |
| Isoform 3 of Fibronectin |
| Glyceraldehyde-3-phosphate dehydrogenase |
| Ceruloplasmin |
| Fructose-bisphosphate aldolase |

| Non-cellular factors |
| --- |
| Isoform 3 of Latent-transforming growth factor beta-binding protein 1 |
| Isoform 2 of Tropomyosin alpha-1 chain |
| Catalase |
| Selenium-binding protein 1 |
| Tropomyosin alpha-1 chain |
| Thrombospondin-3 |
| Peroxiredoxin-1 |
| Tyrosine-protein kinase |
| Antithrombin-III |
| GTP-binding nuclear protein Ran |
| Peroxiredoxin-6 |
| Chloride intracellular channel protein |
| Complement C5a anaphylatoxin |
| Isoform 4 of Tropomyosin alpha-3 chain |
| Tropomyosin alpha-4 chain |
| Protein arginine N-methyltransferase 5 |
| Complement component C7 |
| Chloride intracellular channel protein 1 |
| Carbonyl reductase 3 |
| SPARC |
| Isoform 2 of Ubiquitin carboxyl-terminal hydrolase 14 |
| Vinculin or Isoform 1 of Vinculin |
| C-1-tetrahydrofolate synthase, cytoplasmic |
| Methylenetetrahydrofolate dehydrogenase (NADP+ dependent) 1 |
| Tyrosine-protein kinase |
| Heparin cofactor 2 |
| SPARC |
| Isoform 2 of Coagulation factor IX |
| Ras-related protein Rab-30 |
| Serine/threonine-protein kinase OSR1 |
| RAS like proto-oncogene B |
| Isoform 2 of Adenylyl cyclase-associated protein 1 |
| PDZ and LIM domain protein 1 |
| Coagulation factor IX (Fragment) |
| Talin-1 |
| Fibulin-1 OS = Sus scrofa |
| Serine/threonine-protein phosphatase 2A 65 kDa regulatory subunit A beta isoform (Fragm |
| Isoform 2 of Inter-alpha-trypsin inhibitor heavy chain H3 |
| Glyceraldehyde-3-phosphate dehydrogenase (Fragment) |
| Glutathione peroxidase 3 |
| UMP-CMP kinase |
| Cofilin-1 |
| Peptidyl-prolyl cis-trans isomerase A |
| Coagulation factor XIII A chain |
| Serine/threonine-protein kinase OSR1 |
| RAB7A, member RAS oncogene family |
| 6-phosphofructokinase |
| Superoxide dismutase |
| ADP-ribosylation factor 6 |
| Alpha-soluble NSF attachment protein |
| Eukaryotic initiation factor 4A-III |
| Pyruvate kinase PKM |
| Eukaryotic translation initiation factor 5A-1 |
| Gelsolin |
| Ras-related protein Rab-14 |
| Adenylyl cyclase-associated protein |
| Adenylyl cyclase-associated protein |
| Pyruvate kinase |
| Gelsolin (Fragment) |
| Pyruvate kinase |
| Peroxiredoxin-6 |
| Isoform 3 of Ras-related protein Rap-1b |
| Glyceraldehyde-3-phosphate dehydrogenase |
| Ras-related protein Rab-6B |
| 26S proteasome regulatory subunit 6A |
| ATP-dependent 6-phosphofructokinase, liver type |
| AP complex subunit beta |
| Transitional endoplasmic reticulum ATPase |
| Ras-related protein Rap-1A |
| Pigment epithelium-derived factor |
| T-complex protein 1 subunit zeta |
| T-complex protein 1 subunit delta |

Any one of the agents disclosed above, e.g., anti-thrombotic agents, nutrients, diluent, and $CO_2$-independent buffer system, can be introduced to the diluent (e.g., the physiological solution), and be mixed into the suspension upon dilution of the whole blood. Alternatively or additionally, it can be introduced directly to the whole blood prior to dilution, and/or be introduced to the suspension after dilution of the whole blood.

In certain embodiments, the concentration of a nutrient in the suspension is monitored and adjusted continuously or regularly. In certain embodiments, the nutrient is selected from the group consisting of a monosaccharide (e.g., D-glucose), an amino acid (e.g., a natural amino acid), a vitamin, an inorganic ion, a trace element, and a salt. In a specific embodiment, the concentration of D-glucose in the suspension is monitored during the contacting, and D-glucose is added to the suspension to maintain D-glucose concentration at about 3 to about 11 mmol/L.

In certain embodiments, the concentration of D-glucose in the suspension is monitored by measuring the concentration of D-glucose in a sample collected from the suspension. In certain embodiments, the concentration of D-glucose in the suspension is measured regularly, such as twice every day, once every day, or once every two days. In certain embodiments, the concentration of D-glucose in the suspension is monitored by measuring the concentration of D-glucose using a sensor that is in contact with the suspension. In certain embodiments, the sensor is continuously in contact with the suspension during the contacting. In certain embodiments, D-glucose is added when the measured concentration of D-glucose in the suspension is below 4 mmol/L. In certain embodiments, D-glucose is added to reach a final concentration of about 7 mmol/L; about 8 mmol/L; about 9 mmol/1; or about 10 mmol/L of D-glucose in the suspension. In some embodiments, the glucose levels are adjusted by addition of a 1.1 M D-glucose stock solution. In certain embodiments addition of a 0.91 stock solution (at 1.1M) per mL blood solution leads to an increase of 1 mmol/L in the glucose level. Continuous monitoring by a sensor, optionally in combination with automatic addition of D-glucose in the suspension, allows maintenance of D-glucose concentration in a narrower ranger. Accordingly, in certain embodiments, D-glucose concentration is maintained at about 5 to about 8 mmol/L.

Non-Cellular Blood Factors

In some embodiments, the whole blood sample comprises one or more non-cellular factors, wherein one or more non-cellular factors of the whole blood populate the scaffold, and wherein the one or more non-cellular factors promote cellularization of the acellular tubular scaffold and host compatibility of the vessel upon grafting. As used herein, the term "non-cellular factor" refers to a component in the whole blood suspension that does not comprise a complete eukaryotic cell. A non-cellular factor can be any type of molecule, including but not limited to protein, nucleic acid, saccharide, lipid, small molecule, metal ion, or a conjugate or combination thereof.

For example, the non-cellular factor may be growth factors. In some embodiments, the growth factor is selected from the group consisting of: granulocyte macrophage-colony stimulating factor (GM-CSF), interleukin (IL)-3, IL-4, neutrophin (NT)-6, pleiotrophin (HB-GAM), midkine (MK), interferon inducible protein-10 (IP-10), platelet factor (PF)-4, monocyte chemotactic protein-1 (MCP-1), RANTES (CCL-5, chemokine (C—C motif) ligand 5), IL-8, IGFs, fibroblast growth factor (FGF)-1, FGF-2, FGF-3, FGF-4, FGF-5, FGF-6, FGF-7, FGF-8, FGF-9, transforming growth factor (TGF)-β, VEGF, platelet-derived growth factor (PDGF)-A, PDGF-B, HB-EGF, hepatocyte growth factor (HGF), tumor necrosis factor (TNF)-α, insulin-like growth factor (IGF)-1, and any combination(s) thereof.

In certain embodiments, the non-cellular blood factor is a cell fragment (e.g. thrombocyte, cell fraction). In certain embodiments, the non-cellular blood factor is a protein (e.g., cytokine, chemokine, growth factor, antibody, antibody fragment, protein of the complement system, or enzyme). In certain embodiments, the non-cellular blood factor is a nucleic acid (e.g., circulating DNA, circulating RNA, or circulating miRNA). In certain embodiments, the non-cellular blood factor is a saccharide (e.g., monosaccharide or disaccharide). In certain embodiments, the non-cellular blood factor is a lipid (e.g., fatty acid, triglyceride, or cholesterol). In certain embodiments, the non-cellular blood factor is a small molecule. In certain embodiments, the non-cellular blood factor is metal ion.

In certain embodiments, the non-cellular blood factor is a modified form or a metabolite of any one of the molecules above. For example, in certain embodiments, the non-cellular blood factor is a segment of a protein (e.g., a peptide or polypeptide). In certain embodiments, the non-cellular blood factor is a nucleic acid with one or more modifications (e.g., methylation, 5' capping). In certain embodiments, the non-cellular blood factor is an aldonic acid or alditol of a saccharide. In certain embodiments, the non-cellular blood factor is a sterol. In certain embodiments, the non-cellular blood factor is a conjugate of any one of the molecules disclosed herein, wherein the molecules are conjugated covalently or noncovalently.

In certain embodiments, the concentration of the growth factor is equal to the population average physiological level of the growth factor. In certain embodiments, the concentration of the growth factor is more than the population average physiological level of the growth factor. In certain embodiments, the growth factor is supplemented as an isolated, purified, and/or synthetic molecule.

The non-cellular blood factor can contribute to the reconditioning/recellularization of the acellular tubular scaffold in various ways in vitro or after implantation. For example, in certain embodiments, the non-cellular blood factor promotes attachment or adherence of cells to the scaffold. In certain embodiments, the non-cellular blood factor promotes proliferation of progenitor cells. In certain embodiments, the non-cellular blood factor promotes differentiation of progenitor cells into cells that can populate the scaffold. In certain embodiments, the non-cellular blood factor inhibits apoptosis and/or necrosis of the cells and/or progenitor cells. In certain embodiments, the non-cellular blood factor promotes removal or masking of allogeneic protein(s) present on the scaffold. In certain embodiments, the non-cellular blood factor promotes deposit of autologous protein(s) on the scaffold. In certain embodiments, the non-cellular blood factor promotes conditioning of the scaffold to suppress host rejection.

Contacting the Acellular Tubular Scaffold with Patient Whole Blood

The present disclosure provides a method of preparing a personalized blood vessel, the method comprising contacting the surface (e.g., inner surface) of an acellular tubular scaffold (e.g., a decellularized blood vessel or a bioprinted tubular scaffold) with a suspension comprising whole blood for more than 48 hours, thereby allowing the cells present in the blood to populate the scaffold. In some embodiments, the surface of the acellular tubular scaffold is the inner surface of the acellular tubular scaffold.

As used herein, the term "contact," contacting," or contacted" mean static incubation, perfusion, introducing, injecting, or culturing. Perfusion may be pulsed perfusion, interval perfusion, alternating direction, and no perfusion. In some embodiments, the acellular tubular scaffold is continuously perfused with the suspension or whole blood.

In certain embodiments, the contacting is for more than 2 days. As used herein, the term "more than 2 days" refers to a duration that is longer than 48 hours and longer than about 48 hours. The terms "day" and "days" refer to 24 hour cycle(s). In certain embodiments, the contacting is for at least 3, at least 4, at least 5, at least 6, or at least 7 days. In certain embodiments, the contacting is for up to 9, up to 10, up to 11, up to 12, up to 13, up to 14 days, up to 21 days, or up to 31 days. In certain embodiments, the contacting is for up to 1 month. In some embodiments, the contacting is for from about 1 to 31 days, for 2 to 21 days, for 2 to 14 days, for 2 to 9 days, for 2 to 7 days, for 2 to 5 days, for 5 to 7 days, or for 7 to 9 days. In certain embodiments, the contacting is for about 7 to about 9 days. In some embodiments, contacting the surface of the acellular tubular scaffold is for 2 to 21 days, for 3 to 21 days, for 4 to 21 days, for 5 to 21 days, for 6 to 21 days, or for 7 to 21 days. In certain embodiments, the contacting is for about 2 days, for about 3 days, for about 4 days, for about 5 days, for about 6 days for about 7 days, for about 8 days, for about 9 days, for about 10 days, for about 11 days, for about 12 days, for about 13 days, for about 14 days, for about 15 days, for about 16 days, for about 17 days, for about 18 days, for about 19 days, for about 20 days, or for about 21 days.

The acellular tubular scaffold (e.g., a decellularized blood vessel or a bioprinted tubular scaffold) may be contacted with undiluted whole blood sample or the suspension containing diluted whole blood in any manner known in the art. For example, in certain embodiments, the scaffold is loose and suspended in the suspension, optionally wherein the suspension is shaken (e.g., rotated) to re-mix the components regularly or continuously. Rotation of the tubular scaffold during perfusion may be continuous/intermittent, alternating, or interval.

In certain embodiments, the inner surface of the scaffold is contacted with the suspension. In certain embodiments, the scaffold is perfused with the suspension. In certain embodiments, the scaffold is perfused with a closed recirculation of the suspension. In certain embodiments, the continuous contacting is perfusion conducted using a bioreactor. In certain embodiments, the outer surface of the scaffold is also contacted with the suspension. In other embodiments, the outer surface of the scaffold is not contacted with the suspension. In certain embodiments, the contacting is conducted in vitro.

The perfusion can be conducted in any mode. For example, in certain embodiments, the scaffold is perfused with the suspension continuously. In certain embodiments, the scaffold is perfused with the suspension intermittently (e.g., perfusion for 1 minute at an interval of 4 minutes). In certain embodiments, the perfusion is conducted at a single direction. In certain embodiments, the single direction is the direction of antegrade flow, e.g., the direction allowed by the valve structure(s) in the scaffold. In certain embodiments, the perfusion is conducted at alternating directions (e.g., changing direction every 5 minutes). The speed of the perfusion can be determined by the skilled person in light of a number of factors, such as the diameter of the tubular scaffold, the mechanical strength of the scaffold, the time taken for the cells to sediment, and the viscosity of the suspension. In certain embodiments, the scaffold is perfused at a speed of about 0.1 to about 50 mL per minute. In certain embodiments, the scaffold is perfused at a speed of about 2 ml per minute. Depending on the orientation of the scaffold, rotation during the perfusion (including the intervals) may be advantageous such that the inner surface of the scaffold is populated evenly. In certain embodiments, the scaffold is rotated continuously. In certain embodiments, the scaffold is rotated intermittently (e.g., by 30° every 5 minutes). The direction of the rotation may be constant or alternating. The advantage of rotation may not be substantially where the scaffold is fixed vertically. Accordingly, in certain embodiments, the scaffold is not rotated.

In specific embodiments, the scaffold (e.g., the lumen of the scaffold) is continuously perfused with the suspension. In certain embodiments, the scaffold is perfused at a speed of about 0.1 to about 50 mL per minute (e.g., about 2 mL per minute). In certain embodiments, the scaffold is perfused with a closed recirculation of the suspension. In certain embodiments, the continuous contacting is perfusion conducted using a bioreactor.

Monitoring Environmental Conditions During the Contacting

In another aspect, the present disclosure provides a method of preparing a personalized blood vessel, the method comprising contacting the surface of an acellular tubular scaffold (e.g., a decellularized blood vessel or a bioprinted tubular scaffold) with a suspension comprising whole blood, wherein a plurality environmental parameters (e.g., temperature, pH, oxygen content, and/or $CO_2$ content) are monitored and adjusted continuously or regularly.

In certain embodiments, the contacting is conducted at about 8° C. to about 40° C. In certain embodiments, the contacting is conducted at about 20° C. to about 25° C. In certain embodiments, the contacting is conducted at about 37° C. In certain embodiments, the contacting is conducted at about 20° C., about 21° C., about 22° C., about 23° C., about 24° C., or about 25° C.

In certain embodiments, the contacting is conducted at about pH 7.2 to about pH 7.5. In certain embodiments, the contacting is conducted at about pH 7.4.

In certain embodiments, the contacting is conducted at about 30 mmHg to about 100 mmHg of partial pressure of oxygen. In certain embodiments, the contacting is conducted at about 30 mmHg to about 40 mmHg of partial pressure of oxygen. In certain embodiments, the contacting is conducted at about 80 mmHg to 100 mmHg of partial pressure of oxygen. In certain embodiments, the contacting is conducted at about 160 mmHg of partial pressure of oxygen.

In certain embodiments, the contacting is conducted at about 38 mmHg to about 76 mmHg of partial pressure of carbon dioxide. In certain embodiments, the contacting is conducted at about 38 mmHg of partial pressure of carbon dioxide. In certain embodiments, the contacting is conducted at about 76 mmHg of partial pressure of carbon dioxide. In certain embodiments, the contacting is conducted at about 40 mmHg to about 50 mmHg in of partial pressure of carbon dioxide.

In certain embodiments, the environmental parameters (e.g., temperature, pH, oxygen content, and/or $CO_2$ content) are monitored and adjusted continuously or regularly during the contacting.

In another aspect, the present disclosure provides a method of preparing a personalized blood vessel, the method comprising contacting the surface of an acellular tubular scaffold (e.g., a decellularized blood vessel or a bioprinted tubular scaffold) with a suspension comprising whole blood, wherein the concentration of a nutrient in the suspension is monitored and adjusted continuously or regularly.

In another aspect, the present disclosure provides a method of preparing a personalized blood vessel, the method comprising contacting the surface of an acellular tubular scaffold (e.g., a decellularized blood vessel or a bioprinted tubular scaffold) with a suspension comprising whole blood, wherein the concentration of D-glucose in the suspension is monitored during the contacting, and D-glucose is added to the suspension to maintain D-glucose concentration at about 3 to about 11 mmol/L.

In some embodiments, the concentration of D-glucose in the suspension is monitored by measuring the concentration of D-glucose in a sample collected from the suspension. In some embodiments, the concentration of D-glucose in the suspension is measured once every day. In some embodiments, the concentration of D-glucose in the suspension is monitored by measuring the concentration of D-glucose using a sensor that is in contact with the suspension. In some embodiments, the sensor is continuously in contact with the suspension during the contacting.

In some embodiments, D-glucose is added when the measured concentration of D-glucose in the suspension is below 4 mmol/L. In some embodiments, D-glucose is added to reach a final concentration of 10 mmol/L of D-glucose in the suspension.

Preparation of Acellular Tubular Scaffold with an Enriched or Selected Component of Whole Blood In certain embodiments, the present disclosure provides a method of preparing a personalized blood vessel in which one or more components of whole blood is enriched and selected, and then added to the surface of an acellular tubular scaffold to contact with the inner surface of the scaffold. For example, a component selected from thrombocytes, nucleated cells, proteins, growth factors, signaling factors, immunoglobulins, and any combination(s) thereof, can be added to the inner surface of an acellular tubular scaffold. The component may be enriched or selected by, for example, centrifugation, gradient centrifugation, separation by selective adhesion, filtration, or sorting (e.g., FACS, MACS).

The terms "enriched and selected" refers to a substance and/or entity that has been separated from at least one of the components with which it was mixed when initially produced (whether in nature or in an experimental setting). In certain embodiments, an isolated substance and/or entity is separated from at least 10%, at least 20%, at least 30%, at least 40%, at least 50%, at least 60%, at least 70%, at least 80%, at least 90%, at least 95%, or at least 99% free of the components with which it was mixed when initially produced. In certain embodiments, an enriched and selected substance and/or entity are purified. In certain embodiments, an enriched, selected, and/or purified substance and/or entity is substantially free of other components. As used herein, calculation of percent separation or purity does not include excipients (e.g., buffer, solvent, water, etc.).

Personalized Blood Vessels

The method disclosed herein allows cells and/or progenitor cells to population the surface (e.g., inner surface) of the acellular tubular scaffold (e.g., a decellularized blood vessel or a bioprinted tubular scaffold), thereby generating the personalized blood vessel. In certain embodiments, the cells comprise endothelial cells. In certain embodiments, the cells comprise smooth muscle cells. In certain embodiments, the progenitor cells comprise endothelial progenitor cells. In certain embodiments, the progenitor cells comprise smooth muscle progenitor cells. The skilled person would understand that the cells and/or progenitor cells might populate the scaffold in one or more ways. Population of the scaffold can occur in vitro prior to implantation or in vivo after implantation. In certain embodiments, the cells attach to the scaffold. In certain embodiments, the progenitor cells proliferate and/or differentiate to generate progeny cells, and the progeny cells attach to the scaffold.

In certain embodiments, the contacting results in proliferation and/or differentiation of the progenitor cells to endothelial cells. In certain embodiments, the endothelial cells express VE-cadherin, AcLDL, vWF, and/or CD31. The reconditioned/recellularized scaffold can be characterized for presence of endothelial and smooth muscle cells. Immunohistochemistry and immunofluorescence techniques well known to the ordinarily skilled artisan are utilized to detect the presence or absence of endothelial and smooth muscle cells. To visualize the presence of endothelial cells, antibodies to CD31 (1:200) (Abcam, Germany) and vWF (1:100) (Santa Cruz, Germany) can be used for staining of the reconditioned/recellularized scaffolds. To visualize smooth muscle cells, antibody against smooth muscle actin (1:50) (Abcam, Germany) can be used to stain the reconditioned/recellularized valves. Presence of cells positive of these markers in the recellularized scaffolds are detected by immunohistochemistry or immunofluorescence. Smooth muscle cells can also be identified by the morphology of spindle-shaped muscle cells lining the reconditioned/recellularized scaffolds.

The personalized blood vessels prepared by the method disclosed herein are useful for implantation into a subject (e.g., human). In certain embodiments, the personalized blood vessel is useful as a vein. In certain embodiments, the method further comprises a step of assessing the venous valve function (e.g., using an in vitro valve competence test) of the personalized blood vessel. Exemplary in vitro valve competence tests are provided in U.S. Patent Publication No. 2017/0071738. In certain embodiments, the venous valve function is tested before reconditioning/recellularization. In certain embodiments, the venous valve function is tested after reconditioning/recellularization. In certain embodiments, the venous valve function is tested both before and after reconditioning/recellularization.

A functional personalized blood vessel has no leakage. Accordingly, in certain embodiments, the method further comprises a step of assessing leakage. Various methods are known in the art for testing leakage. For example, in certain embodiments, the personalized blood vessel is flushed with a solution (e.g., a physiologically buffered solution such as phosphate buffered saline (PBS)), preferably at a steady rate, and the surface of the personalized blood vessel is observed for accumulation of solution resulting from a leak or hole. In certain embodiments, leakage is tested before reconditioning/recellularization. In certain embodiments, leakage is tested after reconditioning/recellularization. In certain embodiments, leakage is tested both before and after reconditioning/recellularization.

In another aspect, the present disclosure provides a personalized blood vessel prepared by any one of the methods disclosed herein. In certain embodiments, the personalized blood vessel comprises an acellular tubular scaffold (e.g., a decellularized blood vessel, optionally MMP-treated, or a bioprinted tubular scaffold) including non-cellular factors such as ECM components/composition of a mammalian blood vessel or a functional part thereof, cellularized with human cells (e.g., endothelial cells and/or smooth muscle cells).

The personalized blood vessel of the present disclosure further comprises cells such as, but not limited to, whole blood derived stem or progenitor cells such as endothelial stem cells, endothelial progenitor cells, smooth muscle progenitor cells, whole blood, peripheral blood, and any cell populations that can be isolated from whole blood. The progenitor cells are defined as cells that are committed to differentiate into one type of cells. For example, endothelial progenitor cells mean cells that are programmed to differentiate into endothelial cells; smooth muscle progenitor cells means cells that are programmed to differentiate into smooth muscle cells. Progenitor cells in whole blood or peripheral blood includes population of uncommitted and/or committed cells, such as pluripotent cells or totipotent cells.

In certain embodiments, the surface of the personalized blood vessel is substantially covered by cells. In certain embodiments, the inner surface of the personalized blood vessel is substantially covered by endothelial cells. In certain embodiments, the endothelial cells express VE-cadherin, AcLDL, vWF, and/or CD31.

The skilled person would appreciate that the cells and/or progenitor cells in the blood need not populate the inner surface of the scaffold to the extent that the reconditioned/recellularized scaffold is indistinguishable from native blood vessels. As disclosed herein, recellularization can occur in vitro as well as in vivo post-implantation, and a scaffold partially recellularized in vitro can be further recellularized in vivo to recapture the morphology and/or function of native blood vessels. Notwithstanding, endothelial cells at a lower density than in native blood vessels may also substantially cover the inner surface of the scaffold by adopting a more spread morphology, thereby attaching to a larger surface area per cell.

The personalized blood vessels prepared by the method disclosed herein are useful for implantation into a subject (e.g., human). In certain embodiments, the personalized blood vessel is useful as a vein.

In certain embodiments, the acellular tubular scaffold is derived from a vein (e.g., prepared by decellularizing a native vein). In certain embodiments, the vein is in a lower extremity. The venous system of the lower extremities includes the deep veins, which lie beneath the muscular fascia and drain the lower extremity muscles; the superficial veins, which are above the deep fascia and drain the cutaneous microcirculation; and the perforating veins that penetrate the muscular fascia and connect the superficial and deep veins. Communicating veins connect veins within the same compartment.

In certain embodiments, the vein is a deep vein. Deep veins useful for the instant methods include but are not limited to superficial femoral vein, which connects the popliteal vein to the common femoral vein, and deep veins of the calf (e.g., anterior tibial, posterior tibial, and peroneal veins). In certain embodiments, the vein is a supervicial vein. Deep veins useful for the instant methods include but are not limited to great saphenous vein, the anterior and posterior accessory great saphenous veins, small saphenous vein (SSV), and intersaphenous vein (a.k.a. Giacomini vein).

Most veins have venous valves to assure unidirectional flow of blood. For example, the superficial, deep, and most perforating veins in a lower extremity contain bicuspid valves. Accordingly, in certain embodiments, the acellular tubular scaffold comprises a valve structure, and the valve structure is reconditioned/recellularized to provide a functional venous valve in the personalized blood vessel. The valve structure can be derived either from a native venous valve or from the scaffold synthesis and/or assembly. Methods of assessing the function of a venous valve are known in the art, including but not limited to an in vitro valve competence test. In certain embodiments, the method further comprises assessing the venous valve function (e.g., using an in vitro valve competence test) of the acellular tubular scaffold.

In certain embodiments, the valve structure in the acellular tubular scaffold is reconditioned/recellularized during the reconditioning/recellularization of the rest of the inner surface of the scaffold, i.e., no additional step is taken to specifically recondition/recellularize the valve structure. In certain embodiments, the reconditioned/recellularized valves are CD31-positive. The reconditioned/recellularized valves can also be smooth muscle actin-positive, vWF-positive, and/or be characterized by the presence of spindle-shaped smooth muscle cells.

In certain embodiments, the personalized blood vessel had one or more features of a native blood vessel. In certain embodiments, the personalized vein prepared by a method disclosed herein comprises reconditioned/recellularized valves have mechanical properties of force at first peak above 0.8 N. In certain embodiments, the personalized blood vessel prepared by a method disclosed herein demonstrates no leakage when tested.

Methods of Treatment or Use

In another aspect, the present disclosure provides a personalized blood vessel disclosed herein for use in therapy. In certain embodiments, the present disclosure provides the personalized blood vessel for use in transplantation in a subject. In certain embodiments, the present disclosure provides the personalized blood vessel for use in treating a blood vessel disease or disorder of a subject in need thereof.

The terms "treat," "treating," or "treatment," and other grammatical equivalents as used in this disclosure, include alleviating, abating, ameliorating, or preventing a disease, condition or symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder.

The methods disclosed herein are particularly suitable for generating autologous-like engineered blood vessels. They have the advantages of: (1) being non-immunogenic and therefore having minimal risk of graft rejection or adverse immune response; (2) obviating the need for immunosuppression, and therefore less risk to the patient after surgery and for their lifetime; (3) having no length restriction; (4) being more readily available, as compared to matched donor veins or autologous veins; (5) being composed of natural components (i.e., ECM, endothelial cells and smooth muscle cells), and therefore having superior qualities to mostly synthetic and artificial veins, including preserving residual angiogenic growth factors and biomechanical integrity; 6) requiring invasive production of vein in comparison to harvesting autologous vein for transplant; (7) allowing rapid and minimally invasive procedure to subject by use of whole blood; (8) becoming cellularized and biologically integrated into the subject's body and it's functions (repair, growth, immune-defense).

Accordingly, in one aspect, the present disclosure provides a method of surgery comprising implanting the personalized blood vessel disclosed herein into a subject (e.g., human) in need thereof. In another aspect, the present disclosure provides the personalized blood vessel disclosed herein for use in implantation into a subject (e.g., human) in need thereof. In another aspect, the present disclosure provides a personalized blood vessel prepared by any one of the methods disclosed herein, wherein the personalized blood vessel has been implanted into a subject (e.g., human) by surgery.

In certain embodiments, the personalized blood vessel is autologous. As used herein, the term "autologous" means the blood used in the method of preparing a personalized blood vessel is from the subject receiving the implantation or surgery. In certain embodiments, wherein the personalized blood vessel is produced by decellularizing a native blood vessel, the donor of the native blood vessel is not the same individual as the recipient of the personalized blood vessel. In certain embodiments, wherein the personalized blood vessel is produced by decellularizing a native blood vessel, the native blood vessel is obtained from a suitable animal species (e.g., pig, sheep, cow).

The methods of surgery disclosed herein are useful for treating various vascular diseases or disorders. Accordingly, in certain embodiments, the subject has a vascular disease or disorder, e.g., a venous disease or disorder. In certain embodiments, the venous disease or disorder is selected from the group consisting of deep vein thrombosis (DVT), chronic venous insufficiency (CVI) (a.k.a. postphlebitic syndrome), varicose veins, venous ulceration (e.g., venous leg ulceration), and recurrent leg cancer (e.g., caused by deep venous reflux and/or venous hypertension). In certain embodiments, the personalized blood vessel is implanted, transplanted, or grafted to replace a segment of native blood vessel afflicted with any one of the vascular diseases or disorders. In certain embodiments, the personalized blood vessel is a vein and comprises at least one venous valve.

In certain embodiments, the method of surgery treats, ameliorates, and/or palliates one or more symptoms including dull aching, heaviness, or cramping in legs, itching and tingling, pain that gets worse when standing, pain that gets better when legs are raised, swelling of the legs, redness of the legs and ankles, skin color changes around the ankles, varicose veins on the surface (superficial), thickening and hardening of the skin on the legs and ankles (lipodermatosclerosis), ulcers on the legs and ankles, and wound that is slow to heal on the legs or ankles.

In certain embodiments, the method of surgery disclosed herein treats and/or ameliorates CVI. CVI defines those manifestations of venous disease resulting from ambulatory venous hypertension, defined as a failure to reduce venous pressure with exercise. Under normal circumstances, the venous valves and the muscular pumps of the lower extremity limit the accumulation of blood in the lower extremity veins. Failure of the lower extremity muscle pumps due to out-flow obstruction, musculo-fascial weakness, loss of joint motion, or valvular failure is associated with peripheral venous insufficiency.

In certain embodiments, the method of surgery disclosed herein treats and/or ameliorates venous ulceration. Venous ulcerations are wounds due to improper functioning of the venous valves, usually of the legs (i.e., venous leg ulceration). Venous ulcers arise when valves have reduced function and the backflow of blood causes pooling of blood in the veins and increased pressure in the veins and capillaries. This leads to other related complications, such as edema, inflammation, hardening of the tissue, malnutrition of the skin, and venous eczema. Venous ulcers are large, shallow, discolored due to leakage of iron-containing pigment in red blood cells into the tissue, and may have discharge. The ulcers are most frequently situated around the medial or later malleoli.

In certain embodiments, the method of surgery disclosed herein restores normal lower extremity venous pressure. For example, with walking, lower extremity venous pressure is reduced from approximately 100 mm Hg (depending on height) to mean of 18 mm Hg to about 25 mm Hg within 7 to 12 steps. Similar pressure changes are observed with standing ankle planter flexion or heel rising, transferring weight to the forefoot (the tiptoe maneuver). Ambulatory venous pressure (AVP) can be determined using a 21-gauge needle to measure the response to 10 tiptoe movements, usually at a rate of 1 per second, in dorsal foot vein. When resuming a stating standing position, hydrostatic pressure is restored after a mean of 31 seconds. The incidence of ulceration has a linear relationship to increases in AVP above 30 mm Hg. An increased AVP is also associated with a 90% venous refill time of less than 20 seconds. In contrast to the AVP, volume changes can be measure non-invasively using plethysmography. Rapid reflux (i.e., venous filling of greater than 7 ml/sec) and calf pump dysfunction are associated with a high incidence of ulceration. The reconditioned/recellularized valves in veins, upon grafting, restore the normal AVP, normal rapid reflux and/or normal calf pump dysfunction. Preferably, a venous valve in the personalized blood vessel, upon grafting, restores the normal tolerance of reflux pressure of about 100 mm Hg, and reduces to a mean of about 18 mm Hg to about 25 mm Hg during walking 7 to 12 steps.

In certain embodiments, the method of surgery disclosed herein treats and/or ameliorates the symptoms of incompetent valves in the thigh. In certain embodiments, the treatment and/or amelioration of the symptoms is achieved by restoring normal working relationship between muscle pumps and the venous valves. The muscular pumps of the lower limb include those of the foot, calf, and thigh. Among these, the calf pump is the most important as it is most efficient, has the largest capacitance and generates the highest pressures (200 mm of mercury during muscular contraction). The normal limb has a calf volume ranging from 1500 to 3000 cc, a venous volume of 100 to 150 cc, and ejects over 40% to 60% of the venous volume with a single contraction.

During contraction, the gastrocnemius and soleus muscles drive blood into the large capacity popliteal and femoral veins. The reconditioned/recellularized valves of the present disclosure prevent retrograde flow (reflux) during subsequent relaxation, generating negative pressure and drawing blood from the superficial to the deep system through competent perforating veins. The reconditioned/recellularized valves incrementally lower venous pressure until arterial inflow equals venous outflow. The present disclosure provides that when exercise ceases in a subject, the veins with reconditioned/recellularized valves slowly fill the capillary bed, causing a slow return to the resting venous pressure.

Although muscle surrounds the thigh veins, the contribution of thigh muscle contraction to venous return is minimal compared with the calf muscle pump. Pumping action due to compression of the planter venous plexus during ambulation primes the calf pump. Various leg pumps work together with competent valve function to return venous blood from the distal to proximal extremity. The personalized blood vessels of the present disclosure are for use in restore functional leg pumps to return venous blood from the distal to proximal extremity.

Bioreactors

In another aspect, the present disclosure provides a bioreactor for preparing a personalized blood vessel, the bioreactor comprising a pump (for example a peristaltic pump, a gravity pump, a plunger pump, or other suitable pump), a container, a first connector, and a second connector, wherein the first and second connectors are directly or indirectly connected to the container, wherein each connector is connected to an end of a tubular scaffold for preparing a personalized blood vessel prepared by any one of the methods of preparing a personalized blood vessel disclosed herein, wherein when the first and second connectors are connected to the two ends of a tubular scaffold, the pump mediates the circulation of a suspension, whole blood, or solution in a closed circuit. In many embodiments it is advantageous of a pump (for example a peristaltic pump, a gravity pump, a plunger pump, or other suitable pump) used herein is sufficiently gentle so as to minimize damage to blood cells.

In certain embodiments, the bioreactor further comprises a tubular scaffold (e.g., an acellular tubular scaffold (e.g., a decellularized blood vessel or a bioprinted tubular scaffold)). In certain embodiments, the bioreactor further comprises a suspension or whole blood as disclosed herein for preparing a personalized blood vessel.

In certain embodiments, at least two parts of the bioreactor are provided separately, with an instruction to connect them in the prescribed order. Accordingly, in one aspect, the present disclosure provides a kit for assembling a bioreactor for preparing a personalized blood vessel, the bioreactor comprising a peristaltic pump, a container, a first connector, and a second connector, wherein the first and second connectors can be directly or indirectly connected to the container, wherein each connector can be connected to an end of a tubular scaffold for preparing a personalized blood vessel prepared by any one of the methods of preparing a personalized blood vessel disclosed herein, wherein when the first and second connectors are connected to the two ends of a tubular scaffold, the peristaltic pump mediates the circulation of a suspension, whole blood, or solution in a closed circuit. In certain embodiments, the kit further comprises a tubular scaffold (e.g., an acellular tubular scaffold (e.g., a decellularized blood vessel or a bioprinted tubular scaffold)).

In certain embodiments, the first and second connectors are Luer connectors. In certain embodiments, the first container is directly connected to the container by a tube, and/or the second container is directly connected to the container by a tube.

In certain embodiments, the bioreactor comprises a sampling port. In certain embodiments, the sampling port is a part of the container. In certain embodiments, the sampling port allows withdrawal of a sample of the suspension, whole blood, or solution from the closed circuit. In certain embodiments, the sampling port comprises a sensor for measuring the temperature, pH, and/or the concentration of oxygen, $CO_2$, or nutrient (e.g., D-glucose) in the suspension, whole blood, or solution.

In certain embodiments, the sampling port is also useful as an injection port. In certain embodiments, the bioreactor further comprises an injection port. In certain embodiments, the injection port is or can be connected to a reservoir of oxygen, $CO_2$, or nutrient (e.g., D-glucose).

In certain embodiments, the outer surface of the tubular scaffold is contacted with the suspension, whole blood, or solution in the container. This bioreactor allows reconditioning/recellularization of the inner surface and the outer surface of the tubular scaffold at the same time.

In certain embodiments, the bioreactor further comprises a chamber enclosing the tubular scaffold, thereby allowing contacting of the outer surface of the tubular scaffold with a liquid in the chamber. The chamber can also be sterilized, keeping the tubular scaffold in an aseptic condition.

The skilled person would understand that the same bioreactor could be used for decellularizing a native blood vessel or for conditioning a tubular scaffold. The appropriate suspension, whole blood, or solution can be selected by the skilled person corresponding to the use.

Various pumps can be used, that do not disrupt the cellular and acellular components in the blood solution even during extended periods of perfusion. These can be peristaltic pumps, gravity pumps, piston pumps or similar. The inclusion of sample ports in the bioreactor setup allows sterile sampling of the perfusion medium as well as the sterile injection of additional components without opening the closed loop and in some cases without even stopping the perfusion. In an improved version of the bioreactor setup, sensors a variety of relevant parameters such as glucose, pH, oxygen content, CO2 content, metabolites and so on can be coupled in-line into the perfusion tubing. This allows continuous monitoring of the personalization process during RC or during DC, monitor the progress and success of cell and DNA disruption and removal.

Another aspect of the present disclosure relates to a bioreactor for preparing a personalized blood vessel, the bioreactor comprising a peristaltic pump, a container comprising a sampling port, a first connector, and a second connector, wherein the first and second connectors are directly or indirectly connected to the container, wherein each connector is connected to an end of a tubular scaffold for preparing a personalized blood vessel prepared by the methods disclosed herein, wherein when the first and second connectors are connected to the two ends of a tubular scaffold, the peristaltic pump mediates the circulation of a suspension or solution in a closed circuit.

In some embodiments, the first and second connectors are Luer connectors. In some embodiments, the sampling port is an injection port. In some embodiments, the bioreactor further comprises an injection port. In some embodiments, the injection port is connected to a reservoir of D-glucose. In some embodiments, the first container is directly connected to the container by a tube, and/or the second container is directly connected to the container by a tube. In some embodiments, the bioreactor comprises one or more sample ports. In some embodiments, the bioreactor further comprises one or more sensors for measuring glucose level. In some embodiments, the bioreactor further comprises a pH-adjusting module. In some embodiments, the bioreactor further comprises a $CO_2$ adjusting module.

Another aspect of the present disclosure relates to a method of preparing a personalized blood vessel, the method comprising contacting a surface of an acellular tubular scaffold with a component contained in the whole blood, which is enriched or selected prior to use in contacting the surface.

In some embodiments, the component is selected from thrombocytes, nucleated cells, proteins, growth factors, signaling factors, immunoglobulins, and any combinations thereof.

In some embodiments, the component is enriched by centrifugation, gradient centrifugation, separation by selective adhesion, filtration, or sorting. Many methods for enriching or sorting components are well known in the art. Some example of methods for sorting includes fluorescence activated cell sorting (FACS), magnetic-activated cell sorting (MACS).

Definitions

It is to be understood that methods are not limited to the particular embodiments described, and as such may vary. It is also to be understood that the terminology used herein is for the purpose of describing particular embodiments only, and is not intended to be limiting. The scope of the present technology will be limited only by the appended claims.

As used herein, certain terms may have the following defined meanings. As used in the specification and claims, the singular form "a," "an" and "the" include singular and plural references unless the context clearly dictates otherwise. For example, the term "a cell" includes a single cell as well as a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

The term "about" refers to any minimal alteration in a stated absolute value (e.g., the concentration or amount of an agent) that does not change the stated efficacy, activity, action, results, etc. In embodiments, the term "about" may include ±10% of a specified numerical value or data point. The term "about" includes the stated value (e.g., "about 1%" includes 1% as well as minimal alterations thereof).

Ranges can be expressed in this disclosure as from "about" a first particular value, and/or to "about" a second particular value. When such a range is expressed, another aspect including from the first particular value and/or to the second particular value is also contemplated. Similarly, when values are expressed as approximations, by use of "about," it is understood that the particular value forms another aspect. It is further understood that the endpoints of each of the ranges are significant both in relation to the other endpoint, and independently of the other endpoint. It is also understood that there are a number of values disclosed in this disclosure, and that each value is also disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

EXAMPLES

Example 1: Personalized Tissue Engineered Vein (P-TEV)

Porcine P-TEV grafts were prepared and tested in vivo to show their safety and feasibility. Specifically, pig vena cava was chosen as a substitute model system to mimic the size and thickness of the vessel wall of a human femoral vein.

Preparation of P-TEV

Vena cava was retrieved from pig cadavers and was decellularized to remove the donor cells and DNA. Briefly, the vein segments were perfused sequentially with DC Solution 1, DC Solution 2, and DC Solution 3, with a washing step using sterile water between different DC Solutions. In this example, 24 hours Triton X, 8 h TNBP and 16 h DNase was used. The vein segments were then thoroughly washed with DC Base Solution and PBS for 1 hour and a 48-hour final wash. Next, the vein segments were sterilized in Sterilization Solution, and were thoroughly washed in PBS (1-hour sterilization washes and 48 hour final wash). Each sterile DC vein segment was then transferred to a container with a permanently attached label and frozen at −80° C. in PBS. The compositions of the solutions used in decellularization and sterilization were provided in Table 1.

TABLE 1

Solutions for decellularization and sterilization

| Solution | Composition |
| --- | --- |
| DC Base Solution | Sterile water, 5 mM EDTA |
| DC Solution 1 | 1% Triton X-100 in DC Base Solution |
| DC Solution 2 | 1% Tri-n-butyl phosphate (TNBP) in DC Base Solution |
| DC Solution 3 | 40 U/mL DNase I in PBS with $CaCl_2$ and $MgCl_2$ |
| Sterilization Solution | 0.1% peracetic acid solution in PBS |

The acellularity of the decellularized vein scaffolds was verified by histology with Hematoxylin and Eosin (H&E) staining and 4',6-diamidino-2-phenylindole (DAPI) staining. Specifically, the blue dots in the H&E staining, representing nuclei, were observed in the unprocessed veins but not in the decellularized samples. Similarly, fluorescence from DAPI, indicating DNA, was detectable in the unprocessed veins but not in the decellularized samples. The DNA content of the decellularized vein segments was also evaluated using a Qubit™ fluorometer. The average double-stranded DNA (dsDNA) content of the samples before decellularization was 152 ng per mg of tissue, with a standard error of the mean (SEM) of 32 ng/mg. After decellularization, the samples contained 0.5 ng dsDNA per mg of tissue, with an SEM of 0.04 ng/mg, which was about 0.3±0.03% of the unprocessed material. Therefore, the decellularization rendered the vein scaffolds substantially DNA-free.

To recondition/recellularize the vein scaffolds, peripheral whole blood (PWB) samples were taken from recipient pigs by routine venipuncture in sterile 10 mL BD vacutainer glass tubes containing 17 IU/mL sodium heparin. The PWB was mixed with an ex vivo organ perfusion solution (STEEN™ solution) in a 1:1 ratio, and supplemented with 10 ng/mL of recombinant human FGF-2 (rhFGF-2), 80 ng/mL of recombinant human VEGF (rhVEGF), and 5 µg/mL of acetylsalicylic acid, thereby generating an autologous blood suspension. The reconditioning/recellularization was performed in a closed bioreactor. After prewashing with PBS and pre-treatment with heparin, the vein scaffolds were continuously perfused with the blood suspension in closed recirculation for 7 days. During the perfusion, the glucose level in the blood suspension was maintained between 3-11 mmol/L. Under these conditions, the cellular and other components from the autologous blood suspension repopulated the vein scaffolds.

Surgery

The reconditioned/recellularized P-TEVs were implanted into the recipient pigs by surgery. Specifically, an incision was made through linea alba. A conventional technique to localize vena cava was used for the first two pigs: the intestines were held aside with gauze wetted in saline and surgery hooks, and the part of vena cava between vena renalis and the bifurcation to vena femoralis was dissected free from surrounding tissue. Due to intestinal adhesion formation in one of these two animals, an improved, retroperitoneal technique was used to localize vena cava in the other six pigs (four implanted with P-TEV, two subjected to sham surgery): the peritoneum and the abdominal wall were separated down to vena cava on the dexter side, thereby leaving the intestines untouched. For the P-TEV transplanted pigs, vena cava was cut, and a P-TEV of approximately 4 cm was attached with end-to-end anastomoses. In the sham operated pigs, the tension of the vein did not allow cutting and suturing at two places as with the P-TEV transplants. Instead, vena cava was cut and sutured with one anastomosis.

During the surgery, the pigs were sedated with tiletamine, zolazepam, and medetomidine, and then intubated for anesthesia with isoflurane. Buprenorfin was given during the surgery for post-surgery pain relief. To prevent coagulation and thrombosis, all the pigs were treated perorally with 160 mg acetylsalicylic acid once daily for one week prior to the surgery, and with 2 mg/kg rivaroxaban twice daily from one day pre-surgery until euthanization. Additionally, 10,000 IU heparin was administered intravenously during the surgery.

Conditions of the Pigs after Surgery

Two pigs developed intestinal adhesion after the surgery, and had to be euthanized prior to the planned end point due to ileus symptoms. One was a P-TEV pig in which the vena cava was localized with the conventional technique. It had to be euthanized 16 days post-surgery, and the intestines showed massive adhesions at dissection. The other was a sham pig euthanized 7 days post-surgery. The peritoneum of this pig broke during the surgery, and the intestines had to be handled with wetted gauze and hooks as with the conventional technique.

No intestinal adhesion was observed during dissections of the other six pigs. Among these six animals, one sham pig and three P-TEV pigs were euthanized at the planned end point of 4-5 weeks post-surgery. Two P-TEV pigs had to be euthanized earlier due to complications not related to the vena cava transplantation. One was euthanized 3 days post-surgery, because the sutures of the abdominal wall broke. The other was euthanized 17 days post-surgery because of a knee fracture on the left front leg.

Characterization of the Transplanted P-TEVs

Angiography was performed under anesthesia prior to euthanization of the one sham pig and three P-TEV pigs that were alive 4-5 weeks post-surgery. Contrast fluid was injected into a femoral vein, and the vena cava was monitored live using a C-bow X-ray. As shown in FIGS. 1A-1B, the P-TEV (FIG. 1B) and the sham (FIG. 1A) operated vein were both open with free blood flow.

Following euthanization of each pig, the vena cava was examined. The two sham operated veins and six P-TEVs were all open with free blood flow without sign of clotting or thrombosis. No blood clot or thrombosis was observed at macroscopic examination.

The veins were then sectioned and prepared for H&E staining and DAPI staining. As shown in FIGS. 2A-2B, in the P-TEV (FIG. 2B) pig euthanized 3 days post-surgery, cells were observed in the P-TEV graft by H&E and DAPI staining. The 3-day sample was analyzed as described. Samples after RC were routinely analyzed as well (these represented the last stage of unimplanted P-TEV samples). The P-TEV graft was well cellularized in the pig euthanized 17 days post-surgery. Four to Five weeks after the surgery, the number of cells in the P-TEV (FIG. 2B) appeared to be equal to the native tissue (FIG. 2A). Importantly, intimal hyperplasia, a major potential complication in this study, was not observed in the implanted P-TEV.

Figure 3A:
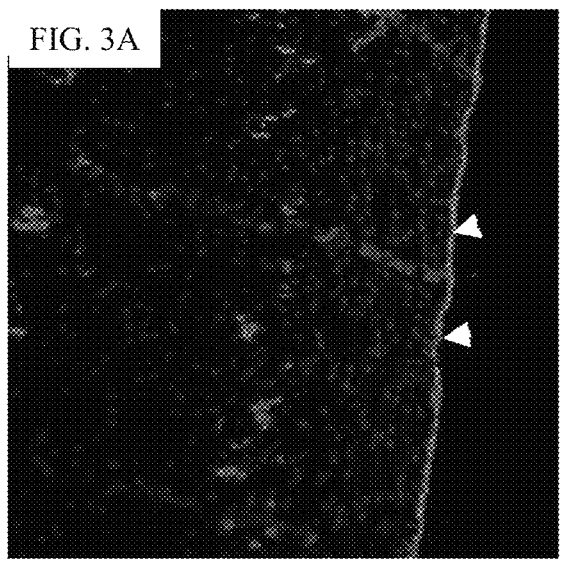
FIGS. 3A-3D depict images showing vena cava cellularization two weeks post surgery.
Figure 3B:
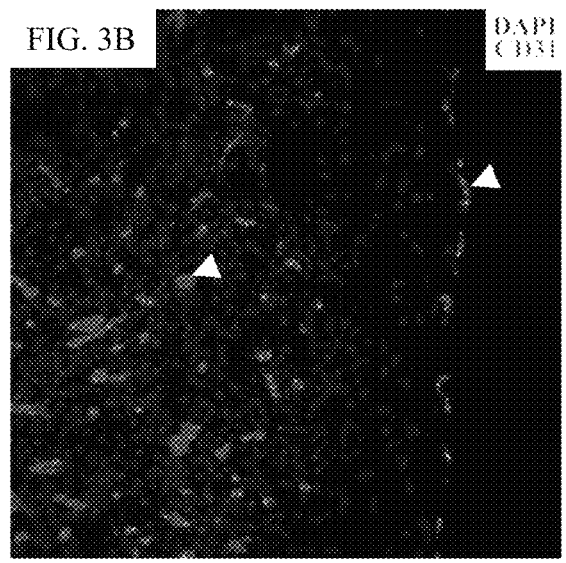
Figure 3C:
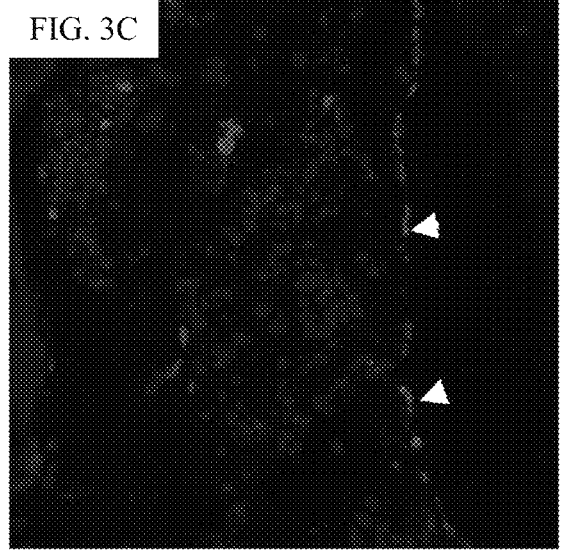
Figure 3D:
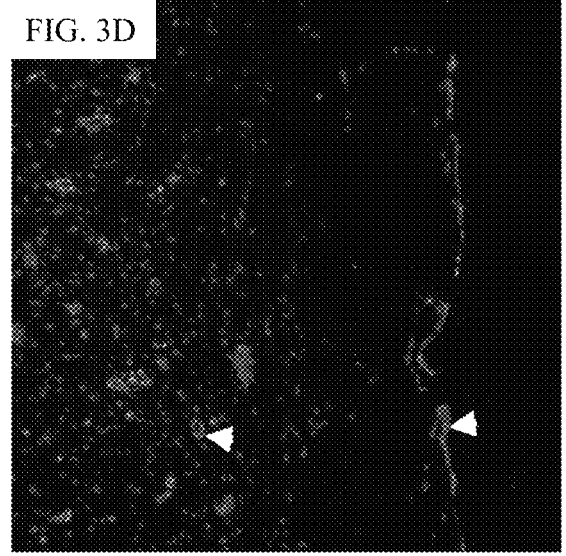

The vein samples were also characterized by immunohistochemistry. In the pig euthanized two weeks post-surgery, the proximal, center, and distal parts of the P-TEV had a substantial number of cells, and CD31-positive cells could be identified (FIGS. 3A-3D). FIG. 3A shows native vena cava proximal to the anastomoses. FIGS. 3B-3D show proximal (FIG. 3B), center (FIG. 3C), and distal (FIG. 3D) parts of the P-TEV. Arrow heads indicate CD31-positive cells.

In a pig euthanized 4-5 weeks post-surgery, the proximal, center and distal parts of the P-TEV had a similar cellular density as the native vena cava, and the P-TEV lumen was covered with a CD31-positive endothelium layer (FIGS. 4A-4D). FIGS. 4A-4D are a series of immunohistograms showing DAPI staining and CD31 immunostaining of vena cava four weeks post-surgery. FIG. 4A shows native vena cava proximal to the anastomoses. FIGS. 4B-4D show proximal (FIG. 4B), center (FIG. 4C), and distal (FIG. 4D) parts of the P-TEV. Arrow heads indicate CD31-positive cells.

Figure 5A:
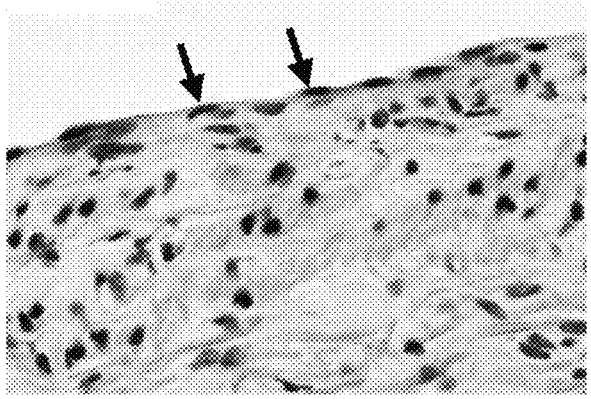
FIGS. 5A-5B depict images showing luminal cell morphology four weeks post surgery.
Figure 5B:
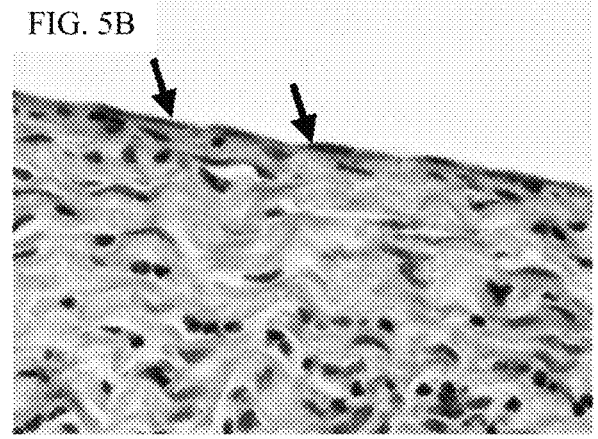

The morphology of endothelial-like cells lining the luminal surface was virtually indistinguishable from that of the native vena cava (FIGS. 5A-5B). FIGS. 5A-5B is a series of images at 40× magnification showing H&E staining of native vena cava (FIG. 5A) and P-TEV transplant (FIG. 5B) four weeks post-surgery. Arrows indicate endothelial cells in the native tissue and cells with plated endothelial cell-like morphology in the P-TEV transplant.

In summary, this in vivo study suggested that the P-TEV were safe and feasible for vein transplantation.

Example 2: Preparation of Physiological Perfusion Solution 900 ml of Dulbeccos Phosphate-Buffered Saline (DPBS) with calcium and magnesium was continuously stirred at 60 rpm at RT. 74 g of Human Serum Albumin were added slowly by layering the powder on the surface of the liquid (to avoid clumping) and stirred until completely dissolved. Foaming was avoided by temporarily reducing the rpm. Subsequently 6.7 g of Dextran-40 were added to the solution and stirred until completely dissolved. The pH was titrated to 7.4 using NaOH and the final volume was adjusted to 1000 ml using DPBS with calcium and magnesium. The physiological perfusion solution is then sterile filtered using a low protein-binding sterile filter, aliquoted into 25 ml aliquots in sterile 50 ml tubes and stored at 2-8° C. for up to 12 months.

Example 3: Preparation of an Alternative Physiological Perfusion Solution (not Requiring Expensive HSA)

25 ml of sterile blood plasma from the patient were placed in a sterile 50 ml tube. 1.5 ml of a 100 g/L sterile-filtered Dextran-40 stock solution were then added to the plasma and the solution was agitated carefully until completely mixed. The sterile physiological perfusion solution was stored at 2-8° C. for up to 7 days.

Example 4: Additional Variations of Prepared Physiological Perfusion Solution DPBS with calcium and magnesium containing 70 g/L HSA, 5 g/L Dextran-40 and 11 mmol/L Glucose DPBS with calcium and magnesium containing 40 g/L HSA and 10 g/L Dextran-40

Human blood plasma containing additional 30 g/L HSA and 5 g/L Dextran-40

Human blood plasma containing additional 5 g/L Dextran-40 and in total 11 mmol/L Glucose DPBS with calcium and magnesium containing 70 g/L HSA, 5 g/L Dextran-60 and 11 mmol/L Glucose

Example 5: Compositions of Commercially Available Physiological Perfusion Solutions

| Solution | Euro Collins | University of Wisconsin | Celsior | Perfadex |
|---|---|---|---|---|
| Colloid Component | Glucose | Lactobionate, Raffinose, Hydroxyethyl starch | Lactobionate, Mannitol | Dextran |
| Buffer | Phosphates, Bicarbonates | Phosphates | Histidine | Phosphates |
| Antioxidant | | Allopurinol, Glutathione | Glutathione, Mannitol | |
| Osmolarity (mOsm/L) | 375 | 330 | 320 | 292 |
| Glucose (mmol/L) | 180 | | | 5 |
| Na$^-$ (mmol/L) | 10 | 25 | 100 | 138 |
| K+ (mmol/L) | 115 | 120 | 15 | 6 |
| Ca$^{2+}$ (mmol/L) | | | 0.25 | |
| Mg$^{2+}$ (mmol/L) | | 5 | 13 | 0.8 |
| Cl$^-$ (mmol/L) | 15 | 20 | | 142 |

Example 6: Preparation of a Personalized Blood Vessel from an Acellular Tubular Scaffold Prepared by Bioprinting Example 1 describes a method of preparing a personalized blood vessel using a decellularized tubular scaffold. Alternatively, a personalized blood vessel is prepared from a bioprinted tubular acellular scaffold. Briefly, the bioprinted blood vessel scaffold is prepared on a polymer (natural or synthetic), which is a gel form, sponge form, foam form, patch form, or a semi-liquid/fluid form. In this method, a polymer scaffold is perfused with whole blood or whole blood diluted in a solution, e.g., a suspension, which includes whole blood, for preparation of a personalized blood vessel.

Example 7: Implantation of Personalized Blood Vessel

A subject in need of a transplanted blood vessel is selected, and a personalized blood vessel prepared by the method provided in Example 1 or 2 of the present disclosure is implanted/transplanted into the subject. The subject's prognosis and recovery post-transplantation is monitored.

An personalized blood vessel disclosed herein is used for treatment of various blood vessel diseases and disorders, such as deep vein thrombosis (DVT), chronic venous insufficiency (CVI), varicose veins, venous ulceration (e.g., venous leg ulceration), and recurrent leg cancer (e.g., caused by deep venous reflux and/or venous hypertension).

Specifically, a subject having a blood vessel disease or disorder is selected. The personalized blood vessel is introduced to the subject by surgery: a segment of native blood vessel afflicted with the disease or disorder is removed; the personalized blood vessel or a functional segment thereof is anastomosed to the native blood vessel, replacing the segment of the native blood vessel that is removed. The hybrid blood vessel generated from the surgery is functionally similar or equivalent as a native blood vessel, and ameliorates the symptoms including dull aching, heaviness, or cramping in legs, itching and tingling, pain that gets worse when standing, pain that gets better when legs are raised, swelling of the legs, redness of the legs and ankles, skin color changes around the ankles, varicose veins on the surface (superficial), thickening and hardening of the skin on the legs and ankles (lipodermatosclerosis), ulcers on the legs and ankles, and wound that is slow to heal on the legs or ankles.

Example 8

The recellularization/reconditioning process of an acellular tubular scaffold for preparing a personalized blood vessel involved a small sample of whole blood from the patient. In this example, the process of recellularization/reconditioning involving cellular as well as non-cellular components (e.g., thrombocytes, nucleated cells, proteins, growth factors, signaling factors, immunoglobulins) of the whole blood are selected or enriched for use in the process. In one example, cellular as well as non-cellular components of the whole blood are combined with whole blood. Alternatively, the cellular as well as non-cellular components of the whole blood are used instead of the whole blood in the recellularization/reconditioning process. The latter process is undertaken for process-related reasons, and/or to optimize the personalization of a blood vessel. Enrichment or selection is performed using, e.g., centrifugation, gradient centrifugation, selective adhesion, chromatography, filtration, or sorting (FACS, MACS).

Other Embodiments

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims. Any definitions provided herein are included for the purpose of understanding the present subject matter and for constructing the appended patent claims. Abbreviations used herein have their conventional meaning within the chemical and biological arts.

What is claimed is:

1. A method of preparing a personalized blood vessel, comprising contacting a surface of an acellular tubular scaffold with a suspension comprising a whole blood sample from a subject in need of the personalized blood vessel, wherein the whole blood sample is diluted in a physiological solution and wherein the contacting is performed for 3 to 14 days.

2. The method of claim 1, wherein a population of cells in the whole blood sample populate the acellular tubular scaffold.

3. The method of claim 1, wherein the whole blood sample comprises one or more non-cellular factors, wherein the one or more non-cellular factors of the whole blood populate the scaffold, and wherein the non-cellular factors promote cellularization of the acellular tubular scaffold and host compatibility of the vessel upon grafting.

4. The method of claim 1, wherein the suspension comprising the whole blood sample further comprises an anti-thrombotic factor.

5. The method of claim 4, wherein the anti-thrombotic factor comprises an anticoagulant agent.

6. The method of claim 5, wherein the anticoagulant agent comprises a heparin or a dextran.

7. The method of claim 6, wherein the heparin is present in the suspension comprising the whole blood sample at a concentration from about 0.5 IU/mL to about 150 IU/mL at the beginning of contacting the surface of the acellular tubular scaffold.

8. The method of claim 7, wherein the heparin is present in the suspension comprising the whole blood sample at a concentration of about 6.7 IU/mL at the beginning of contacting the surface of the acellular tubular scaffold.

9. The method of claim 6, wherein the dextran is dextran-40.

10. The method of claim 6, wherein the dextran is present in the undiluted whole blood sample or the suspension comprising the whole blood sample at a concentration from about 1 g/L to about 55 g/L at the beginning of contacting the surface of the acellular tubular scaffold.

11. The method of claim 4, wherein the anti-thrombotic agent comprises ascorbic acid.

12. The method of claim 11, wherein the ascorbic acid is present in the suspension comprising the whole blood sample at a concentration from about 0.2 µg/mL to about 200 µg/mL at the beginning of contacting the surface of the acellular tubular scaffold.

13. The method of claim 11, wherein the ascorbic acid is present in the suspension comprising the whole blood sample at a concentration of about 5 µg/mL at the beginning of contacting the surface of the acellular tubular scaffold.

14. The method of claim 4, wherein the anti-thrombotic factor comprises acetylsalicylic acid.

15. The method of claim 14, wherein the acetylsalicylic acid is present in the suspension comprising the whole blood sample at a concentration of from about 0.2 µg/mL to about 200 µg/mL at the beginning of contacting the surface of the acellular tubular scaffold.

16. The method of claim 14, wherein the acetylsalicylic acid is present in the suspension comprising the whole blood sample at a. concentration of about 5 µg/mL at the beginning of contacting the surface of the acellular tubular scaffold.

17. The method of claim 1, wherein the suspension comprising the whole blood sample further comprises equal to or more than the population average physiological level of a growth factor selected from the group consisting of: granulocyte macrophage-colony stimulating factor (GM-CSF), interleukin (IL)-3, IL-4, neutrophin (NT)-6, pleiotrophin (HB-GAM), midkine (MK), interferon inducible protein-10 (IP-10), platelet factor (PF)-4, monocyte chemotactic protein-1 (MCP-1), RANTES (CCL-5, chemokine (C-C motif) ligand 5), IL-8, IGFs, fibroblast growth factor (FGF)-1, FGF-2, FGF-3, FGF-4, FGF-5, FGF-6, FGF-7, FGF-8, FGF-9, transforming growth factor (TGF)-β, VEGF, platelet-derived growth factor (PDGF)-A, PDGF-B, HB-EGF, hepatocyte growth factor (HGF), tumor necrosis factor (TNF)-α, insulin-like growth factor (IGF)-1, and any combination(s) thereof.

18. The method of claim 17, wherein the growth factor is a fibroblast growth factor (FGF)-2.

19. The method of claim 1, wherein the contacting is for a period of 3 to 9 days.

20. The method of claim 19, wherein the contacting is for a period of 4 to 9 days.

* * * * *